US008548747B2

(12) United States Patent
Lebo et al.

(10) Patent No.: US 8,548,747 B2
(45) Date of Patent: Oct. 1, 2013

(54) OPTIMIZING GENOME-WIDE MUTATION ANALYSIS OF CHROMOSOMES AND GENES

(75) Inventors: Roger V. Lebo, Akron, OH (US); Aubrey Milunsky, Newton, MA (US); Herman E. Wyandt, Framingham, MA (US)

(73) Assignee: Children's Hospital Medical Center of Akron, Akron, OH (US)

(*) Notice: Subject to any disclaimer, the term of this patent is extended or adjusted under 35 U.S.C. 154(b) by 1981 days.

(21) Appl. No.: 11/244,696

(22) Filed: Oct. 6, 2005

(65) Prior Publication Data

US 2006/0031051 A1 Feb. 9, 2006

Related U.S. Application Data

(62) Division of application No. 10/236,168, filed on Sep. 4, 2002, now abandoned.

(60) Provisional application No. 60/317,007, filed on Sep. 4, 2001.

(51) Int. Cl.
*G01N 33/48* (2006.01)

(52) U.S. Cl.
USPC ............................................................ 702/20

(58) Field of Classification Search
USPC ............................................................ 702/20
See application file for complete search history.

(56) References Cited

U.S. PATENT DOCUMENTS

| | | | |
|---|---|---|---|
| 4,801,531 A * | 1/1989 | Frossard | 435/6 |
| 4,889,819 A | 12/1989 | Davari et al. | |
| 5,023,171 A | 6/1991 | Ho et al. | |
| 5,284,760 A | 2/1994 | Feinstone et al. | |
| 5,286,632 A | 2/1994 | Jones | |
| 5,489,508 A | 2/1996 | West et al. | |
| 5,556,747 A | 9/1996 | Kumar | |
| 5,580,759 A | 12/1996 | Yang et al. | |
| 5,585,362 A | 12/1996 | Wilson et al. | |
| 5,654,148 A | 8/1997 | Lebo | |
| 5,665,540 A | 9/1997 | Lebo | |
| 5,688,677 A | 11/1997 | Ebert et al. | |
| 5,723,593 A | 3/1998 | Lebo et al. | |
| 5,750,571 A | 5/1998 | Cheng et al. | |
| 5,776,677 A | 7/1998 | Tsui et al. | |
| 5,830,645 A | 11/1998 | Pinkel et al. | |
| 5,834,181 A | 11/1998 | Shuber | |
| 5,843,660 A | 12/1998 | Schumm et al. | |
| 5,876,927 A | 3/1999 | Lebo et al. | |
| 5,888,740 A | 3/1999 | Han | |
| 5,989,811 A | 11/1999 | Veltri et al. | |
| 6,197,501 B1 | 3/2001 | Cremer et al. | |
| 6,201,107 B1 | 3/2001 | Lap-Chee et al. | |
| 6,300,073 B1 | 10/2001 | Zhao et al. | |
| 6,352,829 B1 | 3/2002 | Chenchik et al. | |
| 6,358,679 B1 | 3/2002 | Heid et al. | |
| 6,383,749 B2 | 5/2002 | Bochkariov et al. | |
| 6,383,755 B1 | 5/2002 | Davis et al. | |

FOREIGN PATENT DOCUMENTS

| | | |
|---|---|---|
| EP | 0 466 083 A2 | 1/1992 |
| EP | 1026258 A2 | 8/2000 |
| WO | WO 93/21345 | 10/1993 |
| WO | WO 97/43450 * | 11/1997 |
| WO | WO99/16904 A | 4/1999 |

OTHER PUBLICATIONS

Humphries SE. DNA polymorphisms of the apolipoprotein genes—their use in the investigation of the genetic component of hyperlipidaemia and atherosclerosis. Atherosclerosis, vol. 72, 1988, pp. 89-108.*

Lei et al. Genetic basis of glycogen storage disease type Ia: Prevalent mutations at the glucose-6-phosphatase locus. American Journal of Human Genetics, vol. 57, 1995, pp. 766-771.*

Socransky S.S. et al; "Checkerboard DNA-DNA Hybridization" Biotechniques, Informa Life Sciences Publishing, Westborough, MA, U.S. vol. 17, No. 4, (Oct. 1, 1994), pp. 788-792.

Zhenyuan Wang, Jeff Milunsky, Moshe Yamin, Thomas Maher, Robert Oates and Aubrey Milunsky, *Analysis by Mass.Spectrometry of 100 Cystic Fibrosis Gene Mutations in 92 Patients with Congenital Bilateral Absence of the Vas Deferens*, Human Reproduction vol. 17, No. 8 pp. 2066-2072, 2002.

L.C. Williams, M.R. Hegde, G. Herrera, P.M. Stapleton, D.R. Love, *Comparative Semi-Automated Analysis of (CAG) Repeats in the Huntington Disease Gene: Use of Internal Standards*, Molecular and Cellular Probes (1999) 13, 283-289, Article No. mcpr. 1999.0248.

Inge M. Buyse, Ping Fang, Katherine T. Hoon, Ruthie E. Amir, Huda Y. Zoghbi, Benjamin B. Roa; *Diagnostic Testing for Rett Syndrome by DHPLC and Direct Sequencing Analysis of the MECP2 Gene: Identification of Several Novel Mutations and Polymorphisms*, Am. J. Hum. Genet. 67:1428-1436, 2000.

Anthony P. Shuber, Joel Skoletsky, Robert Stern, Barbara L. Handelin, *Efficient 12-Mutation Testing in the CFTR Gene: A General Model for Complex Mutation Analysis*, 6174 Human Molecular Genetics, 2 (1993) Feb., No. 2, Oxford, GB.

Naoyuki Kamatani, Masayuki Hakoda, Sanae Otsuka, Hirofumi Yoshikawa, Sadao Kashiwazaki, *Only Three Mutations Account for Almost all Defective Alleles Causing Adenine Phosphoribosyltransferase Deficiency in Japanese Patients*, Institute of Rheumatology, Tokyo Women's Medical College, Tokyo 162; and Institute of Applied Microbiology, University of Tokyo, Tokyo 113, Japan, J. Clin. Invest, 1992, vol. 90, pp. 130-135.

(Continued)

*Primary Examiner* — Jerry Lin

(74) *Attorney, Agent, or Firm* — Brouse McDowell; Heather M. Barnes

(57) ABSTRACT

Provided is a method of genome-wide testing of gene copy number at the genetically most important loci to determine whether the gene and/or its selected larger surrounding chromosome region is rearranged to result in an unbalanced abnormality in one or more subjects. The method includes selecting multiple gene loci of the DNAs to be examined in the test, conducting the test, and comparing the number of copies at each locus tested by quantification of total gene target number to determine the relative number of each polymorphic sequence detected to assure that each important tested sequence is distinguished from the other alleles at the same locus. A method of detecting the highest number of abnormal patients possible based upon the number of test sites available in a protocol is also provided. Depending upon the state of the life cycle, both of the methods can be done together or in sequence.

16 Claims, 2 Drawing Sheets

(56) References Cited

OTHER PUBLICATIONS

Steffan N. Ho, Henry D. Hunt, Robert M. Horton, Jeffrey K. Pullen, Larry R. Pease, *Site-Directed Mutagenesis by Overlap Extension Using the Polymerase Chain Reaction*, Gene. Apr. 15, 1989;77(1):51-9.

Ke Song-Hua, El Madison—Rapid and Efficient Site Directed Mutagenesis by Single-Tube 'Megaprime' PCR Method Oxford University Press 1995:3371-3372.

David G. Harnden, B. Sc., Ph.D., F.R.C. Path Harold P. Klinger, M.D., Ph.D. An International System for Human Cytogenetic Nomenclature (1985).

R.V. Lebo, H.E. Wyandt, A. Milunsky, Defining DNA Diagnostic Screening Tests Appropriate for Standard-of-Care, Oct. 2004.

Gilles, P.N. et al.; "Single Nucleotide Polymorphic Discrimination by an Electronic Dot Bot Assay on Semiconductor Microchips" Nature Biotechnology, Nature Publishing Group, New York, NY, US, vol. 17, Apr. 1999, pp. 365-370.

Blake et al. Assessment of multiplex florescent PCR for screening single cells for trisomy 21 and single gene defects. Molecular Human Reproduction vol. 5, pp. 1166-1175 (1999).

Wyandt et al. Tandem Duplication/Deletion in a Maternally Dereived Chromosome 9 supernumerary Derivative Resulting in 9p Trisomy and Partial 9q Tetrasomy American Journal of Medical Genetics vol. 93, pp. 305-312 (2000).

Table of Contents, American Journal of Medical Genetics, vol. 93, Issue 4 (Aug. 14, 2000).

Lebo R, Maher T, Farrer L, YUosunkaya Fenerci E, Milunsky J. Highly polymorphic short tandem repeat analyses clarify complex molecular test results. Diagnostic Molecular Pathology, In press, 2001.

Lebo, RV, Shapiro LR, Yosunkaya Fenerci, E, Hoover JM, Chuang JL, Chuang DT, Kronn DF. Denovo mutation and uniparental disomy result in maply syrup urine disase type 2. Am J Hum Genet 67(3):750-754, 2000.

Wyandt H, Lebo R, Yosunkawa Fenerci E, Sadhu DN, Milunsky J. Molecular and cytogenetic characterization of duplication/deletion in a supermumerary der(9) resulting in 9p trisomy and partial 9q tetrasomy. Am J Med Genet 93:305-312, 2000.

Kim H-S, Kilmanskaya IV, Damsky CK, Pedersen RA, Lebo RV. Preimplantation diagnosis of the gamma-1-integrin knockout mutation as a model for gene aneuploid testing. Human Genetics 105(5):480-488, 1999.

Lebo RV, Ikuta, T, Milunsky JM, Milunsky A. Rett Syndrome from quintuple and triple MECP2 gene deletions within the MECP2 deletion hotspot region. Clinical Genetics, 59:406-417, 2001.

Hodge SE, Lebo RV, Yesley AR, Cheney SM, Angle H, Milunsky J. Calculating posterior cystic fibrosis risk with echogenic bowel and one characterized CF mutation. Am J Med Genet 82:329-335, 1999.

Sago H, Kim H-S Goldberg J, Cheung JH, Pedersen R, Lebo RV. Dual blastomere analysis improves reliability of preimplantation trembler mouses diagnosis. Hum Genet 101:223-228, 1997.

Ravnan JB, Chen E, Golabi M, Lebo RV. Fluorescence in situ hybridization detection of chromosome 22q11.2 microdeletions in velocardiofacial syndrome patients with widely variable manifestations. Am J Med Genet 66:250-256, 1996.

Sago H, Goldberg JD, Lebo RV. Point mutation analysis of archived cytogenetic slide DNA. Dytogenet Cell Genet 73:343-346, 1996.

Lapidot-Lifson Y, Lebo RV, Flandermeyer R, Chung J-H, Golbus MS. Rapid aneuploid diagnosis of high risk cases by fluorescence in situ hybridization. Am J Ob Gyn 174:886-890, 1996.

Mansfield ES, Robertson JM, Lebo RV, Lucero MY, Mayrand PE, Rappaport E, Parella T, Sartore M, Surrey S, Fortina P. Duchenne/Becker muscular dystrophy carrier detection using quantitative PCR and fluorescence-based strategies. Am J Med Genet 48:200-208, 1993.

Lebo RV, Lynch ED, Golbus MS, Yen PH, Shapiro L: Prenatal in situ hybridization test deleted steroid sulfatase gene. Am J Med Genet 46(6):652-658, 1993.

Fries MH, Lebo RV, Schonberg S, Golabi M, Seltzer WK, Gitelman SE, Golbus MS: Mental retardation locus in Xp21 chromosome microdeletion. Am J Med Genet 46:363-368, 1993.

Lebo RV, Flandermeyer RR, Lynch ED, Lepercq JA, Diukman R, Golbus M: Prenatal diagnosis with repetitive in situ hybridization probes. Am J Med Genet 43:848-854, 1992.

Lebo RV, Saiki RK, Swanson K, Montano MA, Erlich HA, Golbus MS: Prenatal diagnosis of thalassemia by PCR and dual restriction enzyme analysis. Hum Genet 85:293-299, 1990.

Lebo RV, Golbus MS, Cheung MC: Detecting abnormal human chromosome constitutions by dual-laser flow cytogenetics. Am J Med Genet 25:519-529, 1986.

Lebo RV, Gorin F, Flettrick RJ, Kao F-T, Cheung MC, Bruce BD, Kan YW: High-resolution chromosome sorting and DNA spot-blot analysis localize McArdle's syndrome to chromosome 11. Science 225:57-59, 1984.

Josef Ekstein and Howard Katzenstein: The Dor Yeshorim Story: Community-Based Carrier Screening for Tay-Sachs Disease. Advances in Genetics, vol. 44, pp. 296-311, 2001.

Ying Su, David G. Brooks, Lanying Li, Jacques Lepercq, James A. Trofatter, Jeffrey V. Ravetch and Rober V. Lebo: Myelin protein zero gene mutated in Charcot-Marie-Tooth type 1B patients. Proc. Natl. Acad. Sci., vol. 90, pp. 10856-10860, Nov. 1993.

Snijders A M, Hindle A K, Segraves R, Blackwood S, Myambo K, Yue P, Zhang X, Hamilton G., Brown N, Huey B, Law S, Gray J, Pinkel D, Albertson DG. Quantitative DNA copy number analysis across the human genome with .about.1 megabase resolution using array CGH. Am J Hum Genet 67(4) 31, 2000.

Gardner R J M and Sutherland G R. Chromosome Abnormalities and Genetic Counseling. Oxford Monographs on Medical Genetics No. 29, Oxford University Press, 1996, pp. 87-89.

RM Horton, HD Hunt, SN Ho, JK Pullen, LR Pease—Engineering Hybrid Genes Without the Use of Restriction Enzymes; Gene Splicing by Overlay Extension. Gene. Apr. 15, 1999; 77(1):61-8.

W Ito, H Ishiguro, Y Kurosawa—A General Method for Introducing a Series of Mutations into Cloned DNA Using the Polymerase Chain Reaction Gene. Jun. 15, 1991;102(1):67-70.

RM Horton, ZL Cai, SN Ho, LR Pease—Gene Splicing by Overlap Extension: Tailor-Made Genes Using the Polymerase Chain Reaction Gene. Jun. 15, 1991;102(1):67-70.

SN Ho, HD Hunt, RM Horton, JK Pullen, LR Pease—Site-Directed Mutagenesis by Overlap Extension Using the Polymerase Chain Reaction Gene. Apr. 14, 1989;77(1):51-9.

BN Beck, SN Ho—Increased Specificity of PCR-Amplified Products by Size-Franctionation of Restriction Enzyme-Digested Template Genomic DNA Nucleic Acides Res. Sep. 26, 1988;16(18):9051.

M. Rodriguez, AK Patick, LR Pease, CD David—Role of T Cell Receptor V Beta Genes in Theiler's Virus-Induced Demyelination of Mice J Immunol. Feb. 1, 1992; 148(3):921-7.

H Kadowaki, T. Kadowaki, FE Wondisford, SI Taylor—Use of Polymerase Chain Reaction Catalyzed by Taq DNA Polymerase for Site-Specific Mutagenesis. Gene, Mar. 15, 1989;76(1):161-6.

XJ Yang, CQ Chen, DB Wang, Sly Yang—An Efficient Site-Directed Mutagenesis Using Polymerase Chain Reaction Sci China B. Jun. 1991;34(6):712-8.

Q Liang, L Chen, AJ Fulco—An Efficient and Optimized PCR Method with High Fidelity for Site-Directed Mutagenesis PCR Methods Appl. Apr. 1995:4(5):269-74.

YA Berlin—DNA Splicing by Directed Ligation (SDL) Curr Issues Mol Biol. 1999;1(1-2):21-30.

RM Horton, SN Ho, JK Pullen, HD Hunt, Z Cai, LR Pease—Gene Splicing by Overlap Extension Methods Enzymol. 1993;217:270-9.

S Herlitze, M Koenen—A General and Rapid Mutagenesis Method Using Polymerase Chain Reaction Gene Jul. 2, 1990;91(1):143-7.

K Majumder—Ligation-Free Gene Synthesis by PCR: Synthesis and Mutagenesis at Multiple Loci of a Chimeric Gene Encoding OmpA Signal Peptide and Hirudin Gene. Jan. 2, 1992; 110(1):89-94.

L Young, Q Dong—TAMS Technology for Simple and Efficient in Vitro Site-Directed Mutagenesis and Mutant Screening Nucleic Acids Res. Feb. 1, 2003;31(3):e11.

MM Ling, BH Robinson—Approaches to DNA Mutagenesis: An Overview Anal Biochem. Dec. 15, 1997;254 (2):157-78.

F Allemandou, J Nussberger, Hr Brunner, N. Brakch—Rapid Site-Directed Mutagenesis Using Two-PCR-Generated DNA Fragments Reproducing the Plasmid Template J Biomed Biotechnol. 2003;2003(3):202-207.

A Seyfang, JH Jin—Multiple Site-Directed Mutagenesis of More than 10 Sites Simultaneously and in a Single Round Anal Biochem. Jan. 15, 2004;324(2):285-91.

AN Vallejo, RJ Pogulis, LR Pease—in Vitro Synthesis of Novel Genes: Mutagenesis and Recombination by PCR PCR Methods Appl. Dec. 1994; 4(3):S123-30.

GJ Rouwendal, EJ Wolbert, LH Zwiers, J Springer—Simultaneous Mutagenesis of Multiple Sites: Application of the Ligase Chain Reaction Using PCR Products Instead of Oligonucleotides Biotechniques. Jul. 15, 1993;(1):68-70, 72-4, 76.

S Byrappa, DK Gavin, KC Gupta—Highly Efficient Procedure for Site-Specific Mutagenesis of Full-Length Plasmids Using Vent DNA Polymerase Genome Res. Nov. 5, 1995(4):404-7.

SD Senanayake, DA Brian—Precise Large Deletions by the PCR-Based Overlap Extension Method Mol Biotechnol. Aug. 4, 1995(1):13-5.

W Wang, BA Malcolm—Two-Stage Polymerase Chain Reaction Protocol Allowing Introduction of Multiple Mutations, Deletions, and Insertions, Using QuikChange Site-Directed Mutagenesis Methods Mol Biol. 2002;182-37-43.

SH, KE, EL Madison—Rapid and Efficient Site-Directed Mutagenesis by Single-Tube Megaprimer: PCR Method Nucleic Acids Res. Aug. 15, 1997;25(16):3371-2.

RJ Pogulis, AN Vallejo, LR Pease—In Vitro Recombination and Mutagenesis by Overlap Extension PCR Methods Mol Biol. 1996;57:167-76.

A Aiyar, Y Xiang, J Leis—Site-Directed Mutagenesis Using Overlap Extension PCR Methods Mol Biol. 1996;57:177-91.

I Rabhi, N. Guedel, I Chouk, K Zerria, MR Barbouche, K Dellagi, DM Fathallah—A Novel Simple and Rapid PCR-Based Site-Directed Mutagenetis Method. Mol Biotechnol. Jan. 26, 2004(1):27-34.

NA Shevchuk, AV Brysin, YA Nusinovich, FC Cabello, M Sutherland, S Ladisch—Construction of Long DNA Molecules Using Long PCR-Based Fusion of Several Fragments Simultaneously Nucleic Acids Res. Jan. 22, 2004;32(2):e19.

GJ Chang, BJ Johnson, DW Trent—Site-Specific Oligonucleiotide-Directed Mutagenesis Using T4 DNA Polymerase DNA. Apr. 7, 1988(3):211-7.

A Urban, S Neukirchen, KE Jaeger—A Rapid and Efficient Method for Site-Directed Mutagenesis Using One-Step Overlap Extension PCR Nucleic Acids Res. Jun. 1, 1997;25(11):2227-8.

F Vallette, E Mege, A Reiss, M Adesnik—Construction of Mutant and Chimeric Genes Using the Polymerase Chain Reaction Nucleic Acids Res. Jan. 25, 1989;17(2):723-33.

RM Nelson, GL Long—A General Method of Site-Specific Mutagenesis Using a Modification of the Thermus Aquaticus Polymerase Chain Reaction Anal Biochem. Jul. 1989;180(1):147-51.

DH Jones, BH Howard—Rapid Method for Recombination and Site-Specific Mutagenesis by Placing Homologous Ends on DNA Using Polymerase Chain Reaction Biotechniques. Jan. 1991;10(1):62-6.

Landt, HP Grunert, U Hahn—A General Method for Rapid Site-Directed Mutagenesis Using the Polymerase Chain Reaction Gene. Nov. 30, 1990;96(1):125-8.

RM Horton—PCR-Mediated Recombination and Mutagenesis. SOEing Together Tailor-Made Genes Mol Biotechnol. Apr. 1995;3(2):93-9.

DH Jones, SC Winistorfer—Recombinant Circle PCR and Recombination PCR for Site-Specific Mutagenesis Without PCR Product Purification. Biotechniques. Apr. 1992;12(4):528-30, 532, 534-5.

HG Morrison, RC Desrosiers—A PCR-Based Strategy for Extensive Mutagenesis of a Target DNA Sequence Biotechniques. Mar. 1993;14(3):454-7.

RD Kirsch, E Joly—An Improved PCR-Mutagenesis Strategy for Two-Site Mutagenesis or Sequence Swapping Between Related Genes Nucleic Acids Res. Apr. 1, 1998,26(7):1848-50.

A.M. Ali Inan, George P. Patrinos, Mariken De Krom, Stefania Bottardi, Rick J. Janssens, Eleni Katsantoni, Albert W. K. Wai, David J. Sherratt, Frank G. Grosveld—Modification of human B-globin locus PAC clones by homologous recombination in *Escherichia coli*. Biotechniques. Jul. 1993:15(1):68-70, 72-4, 76.

Weiner MP, Costa GL—Rapid PCR site-directed mutagenesis. Methods Mol Biol. 1996;57:167-76.

ZB Nagy, F. Felfoldi, L. Tamas, LG Puskas—A one-tube, two-step polymerase chain reaction-based site-directed mutagenesis method with simple identification of the mutated product. Analytical Biochemistry 324 (2004) 301-303.

Riordan et al., Identification of the cystic fibrosis gene: cloning and characterization of complementary DNA. Science 245:1066-1073, 1989.

Milunsky J M, Lebo R V, Ikuta T, Maher T A, Haverty C E, Milunsky A. Mutation Analysis in Rett Syndrome. Genetic Testing 5(4):321-325, 2001.

SL Berger, RE Manrow, HY Lee—Phoenix Mutagenesis: One-Step Reassembly of Multiply Cleaved Plasmids with Mixtures of Mutant and Wild-Type Fragments Anal Biochem. Nov. 1, 1993;214(2):571-9.

Q Mo, X Xu, X Zhong, Z Liu—An Improved PCR-Based Megaprimer Method for Site-Directed Mutagenesis Zhonghua Yi Xue Yi Chuan Xue Za Zhi. Feb. 2002;19(1):68-71.

Lebo RV, Milunsky J, Loose B, Huang X-L, Wyandt H. Symmetric replication of an unstable isodicentric Xq chromosome derived from isolocal maternal sister chromatid recombination. Am J Med Genet 85:429-437, 1999.

R.V. Lebo, H.E. Wyandt, A Milunsky, Defining DNA Diagnostic Screening Tests Appropriate for Standard-of-Care. Abstract, The American Society of Human Genetics, 54th Annual Meeting, Oct. 26-30, 2004, p. 278.

Ohnishi A, Li L-Y, Fukushima Y, Mori T, Mori M, Endo C, Yoshimura T, Sonobe M, Flandermeyer R, Lebo RV. Asian hereditary neuropathy patients with peripheral myelin protein-22-gene aneuploidy Am J Med Genet 59:51-58, 1995.

Lebo R V, Martelli L, Su Y, Li L-Y, Lynch E, Mansfield E, Pua K, Watson D, Chueh J, Hurko O: Prenatal diagnosis of Charcot-Marie-Tooth disease Type 1A by multicolor in situ hybridization. Am J Med Genet 47(3):441-450, 1993b.

Snijders A M, Hindle A K, Segraves R, Blackwood S, Myambo K, Yue P, Zhang X, Hamilton G., Brown N, Huey B, Law S, Gray J, Pinkel D, Albertson DG. Quantitative DNA copy number analysis across the human genome with about 1 megabase resolution using array CGH. Am J Hum Genet 67(4) 31, 2000.

Herbergs J, Smeets E, Moog U, Tserpelis D, Smeets H. MECP2 mutation analysis and genotype/phenotype correlation in 26 Dutch Rett syndrome patients. Am J Hum Genet 69(4):306, 2001.

Office Action for U.S. Appl. No. 10/236,168, Mar. 24, 2006, 14 pages.

Office Action for U.S. Appl. No. 10/236,168, Jul. 28, 2005, 7 pages.

Office Action for U.S. Appl. No. 11/244,697, Jun. 26, 2009, 9 pages. This application will be abandoned.

Office Action for U.S. Appl. No. 11/244,697, Aug. 8, 2008, 8 pages. This application will be abandoned.

Office Action for U.S. Appl. No. 11/244,697, Apr. 8, 2008, 5 pages. This application will be abandoned.

Office Action for Canadian Application No. 2,455,607, Nov. 4, 2005, 3 pages.

Office Action for Canadian Application No. 2,455,607, Oct. 31, 2006, 4 pages.

Office Action for Canadian Application No. 2,455,607, Oct. 2, 2008, 3 pages.

Office Action for European Application No. 02 806 718.9-1222, Oct. 9, 2007, 4 pages.

Office Action for European Application No. 02 806 718.9-1222, Feb. 10, 2009, 7 pages.

Supplementary European Search Report for European Application No. 02 806 718.9-1222, Feb. 1, 2007, 3 pages.

Gilles, P.N. et al, Single Nucleotide Polymorphic Discrimination by an Electronic Dot Blot Assay on Semiconductor Microchips, Nature Biotechnology, Nature Publishing Group, New York, NY US, vol. 17, Apr. 1999, pp. 365-370.

Roger V. Lebo, Ph.D., Michelle Bixler, Donna Galehouse, Ph.D., One Multiplex Control for 29 Cystic Fibrosis Mutations, Genetic Testing, vol. 11, No. 2, 2007.

* cited by examiner

FIG-1E  TETRAPLOID – 3 SPERM, 1 EGG

FIG-1F  TETRAPLOID – ABNORMAL MITOSIS

FIG-1G  TRIPLOID – 2 SPERM + 1 EGG or 2 EGG + 1 SPERM

*SRY, ZFY, AMEL Y

OPTIMIZING GENOME-WIDE MUTATION ANALYSIS OF CHROMOSOMES AND GENES

CROSS REFERENCE TO RELATED APPLICATIONS

This application claims the priority of utility application having Ser. No. 10/236,168 filed on Sep. 4, 2002, which claims priority to U.S. Provisional Application Ser. No. 60/317,007 filed Sep. 4, 2001 entitled "Genome-Wide Aneuploid Analysis of Chromosomes and Genes" by QPCR the whole of which is hereby incorporated by reference herein.

BACKGROUND OF THE INVENTION

Since the early 1970's when routine chromosome banding was developed, Giemsa-banded chromosome analysis has been applied to diagnosing chromosome abnormalities in fetuses, abnormal children, adolescents, and adults, in both normal and neoplastic tissues. Giemsa-banded karyotypes will detect abnormal chromosomes in about 644 newborns among every 100,000 births (Lebo et al, 1992). Banded chromosome analysis is time consuming and requires considerable training and expertise from growing the cells and preparing slides of well separated, banded chromosomes, to recognizing and analyzing spreads of randomly mixed metaphase banded chromosomes from selected cells for whole and partial chromosome abnormalities. Nevertheless, chromosome banding identifies only about half of all genetic abnormalities because the limit of light microscope resolution is on the order of 5,000,000 basepairs of DNA (5 Mb spanning an average of 50 genes) that must be modified in order to detect a change in the chromosome banding pattern. In contrast, molecular testing can use sampled cells that have not grown outside the body, complete analysis in hours rather than days, and distinguish the modification of a single basepair change or quantify the number of target gene sequences that may have changed within a normal appearing banded chromosome. With the exception of chromosome banding, a single format has not been applied successfully to genome-wide screening.

Initially we conceived and developed a screening test for aneuploidy of five chromosomes (13, 18, 21, X, and Y) that result in 95% of chromosomally abnormal newborns (Lebo et al, 1992). This test has been modified by other investigators to enumerate chromosome 13 and chromosome 21 independently and with simultaneous commercialization and wider testing validation by Vysis has received FDA approval. Today this is used for late gestation fetuses to determine rapidly whether a fetus with an abnormal ultrasound has one of these viable chromosome aneuploidies in order to optimally plan delivery (Lapidot-Lifson et al, 1996) and to obtain a rapid result for earlier gestation pregnancies undergoing triple screen analysis. G-banded karyotypes are still completed routinely on all sampled fetal cells (amniocytes or chorionic villus cells).

Considering these developments, our initial patent application suggested selecting carefully chosen genome-wide chromosome sites to be tested for aneuploidy in order to detect the largest proportion of chromosome rearrangements resulting in partial or full chromosome aneuploidy, and to test for all additional submicroscopic and microscopic deletions that commonly result in genetic disease because this would be a more rapid test that detected a larger number of abnormal fetuses than Giemsa-banded karyotyping (Lebo et al., Provisional 60/161857). As we have continued to work on this approach, we designated the most common gene mutations to be tested simultaneously to detect the largest number of genetic abnormalities possible in a single test on a minimal size testing format.

More recently Snijders et al., (2000) applied CGH to segments of chromosomes at 1 Mb regions in order to detect aneuploid (absence of two) copies of each location reflecting chromosome rearrangement. This requires >2,000 sites to test the 3,000,000,000 basepair haploid human genome at ~1 megabase intervals. Two difficulties were not anticipated using this approach: (1) the greater the number of sites tested, the greater the likelihood that an error will occur given the same error frequency at each tested site, and (2) tested sites were designated according to physical distance rather than selecting genetically important sites that when mutated result in the most common disease-causing mutations. Thus a large proportion of normal patients tested at these >2000 sites have deleted chromosome regions that merely reflect normal polymorphic variability (Alfred Mazzocchi, Vysis Molecular specialist-Midwest, Pers. Comm., August, 2002). Therefore this approach requires determining the normal polymorphic variability in the general population and the restructuring of the sites selected.

The cystic fibrosis gene is mutated by any one of over 1000 mutations carried by 1 in 29 Caucasians. Over two dozen laboratories offer routine cystic fibrosis testing for 12 to 100 cystic fibrosis mutations. The number of mutation tests offered reflect not only the frequency each mutation is found within the tested population but also differences in the laboratory's prior experience in identifying specific cystic fibrosis mutations, and the likelihood of test referral from genetics professionals based upon the number of tested mutations. The economic principle of "diminishing returns" states that when any factor is increased while other factors are held constant in amount, the gain in benefit beyond a certain point will diminish for each additional unit of resources invested. Given an ever larger number of mutations tested and an equal probability of error on each single mutation test provided, the probability of laboratory error could exceed the likelihood of finding any tested mutation. Given that most cystic fibrosis mutations are extremely rare and the likelihood of making a laboratory error may exceed the likelihood of finding a rare mutation, the American College of Medical Genetics committee on cystic fibrosis testing decided that testing the 25 mutations found in >0.1% of the cystic fibrosis mutant alleles in all Caucasions is to be considered standard-of-care for all testing laboratories. Selecting these 25 mutations opened the opportunity for the best laboratories to test other common disease gene mutations that detect many more abnormal alleles than tests for very rare alleles at one gene site. Reflex gene mutation or sequencing tests provide the opportunity to complete the most reliable diagnoses in higher-risk patient populations.

The following references are relevant as background to the present invention:

Lebo R V, Saiki R K, Swanson K, Montano M A, Erlich H A, Golbus M S: Prenatal diagnosis of α-thalassemia by PCR and dual restriction enzyme analysis. Hum Genet 85:293-299, 1990.

Lebo R V, Lynch E D, Golbus M S, Yen P H, Shapiro L: Prenatal in situ hybridization test for deleted steroid sulfatase gene. Am J Med Genet 46(6):652-658, 1993a.

Lebo R V, Martelli L, Su Y, Li L-Y, Lynch E, Mansfield E, Pua K, Watson D, Chueh J, Hurko O: Prenatal diagnosis of Charcot-Marie-Tooth disease Type 1A by multicolor in situ hybridization. Am J Med Genet 47(3):441-450, 1993b.

Mansfield E S. Diagnosis of Down syndrome and other aneuploidies using quantitative polymerase chain reaction and small tandem repeat polymorphisms. Hum Molec Genet 1992; 2:43-50.

Pinkel D, Albertson D, Gray J W, Comparative fluorescence hybridization to nucleic acid arrays. U.S. Pat. No. 5,830,645. Nov. 3, 1998.

Riordan et al., "Identification of the cystic fibrosis gene: cloning and characterization of complementary DNA. Science 245:1066-1073, 1989.

Snijders A M, Hindle A K, Segraves R, Blackwood S, Myambo K, Yue P, Zhang X, Hamilton G., Brown N, Huey B, Law S, Gray J, Pinkel D, Albertson D G. Quantitative DNA copy number analysis across the human genome with ~1 megabase resolution using array CGH. Am J Hum Genet 67(4) 31, 2000.

Wyandt H, Lebo R, Yosunkawa Fenerci E, Sadhu D N, Milunsky J. Molecular and cytogenetic characterization of duplication/deletion in a supernumerary der(9) resulting in 9p trisomy and partial 9q tetrasomy. Am J Med Genet 93:305-312, 2000.

Lebo R V, Flandermeyer R R, Lynch E D, Lepercq J A, Diukman R, Golbus M: Prenatal diagnosis with repetitive in situ hybridization probes. Am J Med Genet 43:848-854, 1992.

Gardner R J M and Sutherland G R. Chromosome Abnormalities and Genetic Counseling. Oxford Monographs on Medical Genetics No. 29, Oxford University Press, 1996, pp. 87-89.

Milunsky J M, Lebo R V, Ikuta T, Maher T A, Haverty C E, Milunsky A. Mutation Analysis in Rett Syndrome. Genetic Testing 5(4):321-325, 2001.

Herbergs J, Smeets E, Moog U, Tserpelis D, Smeets H. MECP2 mutation analysis and genotype/phenotype correlation in 26 Dutch Rett syndrome patients. Am J Hum Genet 69(4):306, 2001.

Lebo R V, Flandermeyer R R, Lynch E D, Lepercq J A, Diukman R, Golbus M: Prenatal diagnosis with repetitive in situ hybridization probes. Am J Med Genet 43:848-854, 1992.

Milunsky J M, Lebo R V, Ikuta T, Maher T A, Haverty C E, Milunsky A. Mutation Analysis in Rett Syndrome. Genetic Testing 5(4):321-325, 2001.

SUMMARY OF THE INVENTION

This invention increases the proportion of informative tests for whole or partial chromosome aneuploidy or gene aneuploidy over current methods by using quantitative gene region analysis to (1) unambiguously characterize aneuploidy of chromosomes 13, 18, 21, X and Y that result in a majority of the phenotypic chromosome abnormalities in fetuses and newborns, (2) expand testing to detect other microscopic or submicroscopic partial chromosome imbalances in 30 additional chromosome regions, (3) test genetic diseases resulting from unique gene aneuploidy including, and (4) to readily add testing for the most common gene mutations in the patient's ancestral population. Detecting the second category of gene imbalance will increase the frequency of prenatal chromosome abnormalities that are detected rapidly in Category 1 from 95% of phenotypically significant chromosome abnormalities in newborns (Lebo et al, 1992) to 98%, while also adding category (3) will provide a total pickup of 102% of the number detected by current Giemsa-banded chromosome analysis. This includes testing for the 7 common deleted dystrophin gene regions to detect about 60% of the dystrophin gene mutations in affected male fetuses found at a frequency of about 1 in 20,000 live births in families with no prior family history with the ability to determine these results from a direct fetal cell sample without cell culture, DNA analysis is predicted to be more clear-cut than the rapid screening Combined interphase in situ hybridization test and when sufficiently reliable is likely to replace karyotyping as the screening test of choice. The fourth test category will optimize genome-wide screening for the most common genetic disease mutations in the target population. Combining the most common chromosome abnormalities that can be tested with the most common gene mutations will detect even more major genetic abnormalities than standard amniocentesis. At the same time, testing for other common mutations like the 8 common Rett gene point mutations will detect two-thirds of the viable fetuses with Rett syndrome which affects about 1 in 12,000 (Herbergs et al, 2001) with about 99% of affected fetuses carrying de novo mutations (Milunsky et al, 2001). Adding 8 Rett sites to be tested will detect 103% of abnormalities detected by G-banded karyotypes and require testing 46 selected assays around the genome. Selection of the sites to be tested can be modified depending upon new data and the target population and the frequency of each mutation compared to other individual mutations within the population. Individual mutation frequencies are calculated according to the frequency of the genetic disease and the frequency that each mutation contributes to the total number of mutations that result in that disease. Simultaneously testing these categories of genetic diseases will provide the most optimal genetic screening tool for fetuses, newborns, pregnant couples, and aging patients undergoing routine physical examinations in order to provide optimal lifelong care. As these tests become less expensive and more inclusive, formats can be tailored to different populations throughout the world where specific genetic diseases are common that are not screened in other populations.

With the present invention, the construction and application of a genome-wide screen that selects and tests the most common chromosomal regions that when unbalanced result in a viable abnormal newborn. Unbalanced gametes and zygotes result from whole chromosome aneuploidy (abnormal number), unbalanced translocations (unbalanced reciprocal chromosome segment switches), deletions, insertions, marker chromosomes (extra partial chromosomes), and more complex rearrangements. Balanced gametes with the correct total gene number result from balanced translocations and inversions (changing the order of some genes within the chromosome). Testing 27 selected chromosome regions that when unbalanced most commonly result in viable abnormal newborns would identify an estimated 98% of chromosome rearrangements that result in phenotypic abnormality in newborns. Site selection within these chromosome regions also depends upon the means used to test the number of DNA targets i.e. (1) polymorphisms tested by hybridization to target DNA sequences or observed after visualization to distinguish quantity between unique polymorphic (normally variable) alleles, or (2) hybridization to large nonvariable target DNA sequences. Sites are specifically avoided that encode a normal phenotype even when unbalanced to simplify test interpretation and minimize reflex testing and turn around time. Selection of the chromosome sites will be according to: (1) the published common aneuploid chromosome regions resulting in abnormal newborns, (2) additional sites that increase the frequency of pickup of abnormality according to the limit of the assay format used, and (3) the common gene mutation and deletion sites of the most common genetic diseases tested in the patient's ancestral population.

Herein we present one preferred genome-wide testing embodiment with a core of 27 selected chromosome sites for prenatal testing to detect about 98% of the phenotypical abnormal newborns among the 644 chromosome abnormalities found per 1,000,000 newborns. Another 11 common submicroscopic deletion/duplication sites including Dystrophin, SNRPN, PMP22 and ELN gene sites to be tested (38 total) to detect submicroscopic de novo mutations resulting in identifying 2% more fetuses with a genetic disease than Giemsa-banded karyotyping or quantification of >2,000 evenly spaced cloned genomic sites (Snijders et al, 2000). It has not escaped our attention that although the abnormal neoplastic karyotypes have common chromosome rearrangements related to cell growth that differ entirely from the fetal karyotypes, the same principles of testing selected modified gene sites will also be superior to testing sites selected arbitrarily according to evenly spaced physical locations on the chromosomes. In fact, the evenly spaced format of evenly spaced physical locations on the chromosomes. In fact, the evenly spaced format of Snijders is quite useful in helping to identify gene locations that are commonly mutated in neoplastic progression. However, after these genes have been identified, the most robust tests are of the genes or gene products themselves.

Molecular genetic testing is becoming ever more important in prenatal diagnosis, maternal and newborn screening, screening for genetic disease in symptomatic and at-risk patients, identity and paternity testing, characterizing disease-causing organisms contracted from others or released by terrorists, characterizing recombinant genes in food, confirming the pedigrees of animals or plants, and identifying criminals. Currently greater than 800 molecular genetic tests are offered in laboratories around the world. Typically each test is offered individually while multiple required tests might need to be submitted to multiple laboratories to be completed. Offering a screening test for the most common abnormal alleles is the most efficacious method of screening patients in the population and designating which patients should be tested by the more complex kayotyping and specific disease tests offered in many laboratories.

A corollary to this approach is that screening any group of at-risk individuals for molecular genetic diseases should be based upon the frequency of the common gene mutations in the population. When the frequencies are determined by multiplying the frequency of the disease times the frequency of mutations for each specific DNA alteration, these frequencies can be listed from most common to least common. Then any molecular genetic test format that is developed can simply move down the list as far as the number of mutations that can be tested reliably, simply, and cost effectively given the test format. This will screen for the largest number of genetic disease genes. The list will vary according to the age, clinical status, and race of the at-risk patient being tested. For all mutations found in the heterozygous state for autosomal recessive genetic diseases, disease-specific reflex tests would be offered.

The present invention also contemplates the use of kits that contain multiple allelic site primer sequences in a few tubes that can be aliquoted and tested as a multiplex test. This provides a convenient way of employing the genome-wide screens of the present invention.

An object of the present invention is to provide a method of simultaneously testing for a plurality of sets of chromosomal anomalies, each set corresponding to one or more anomalies and mutations that result in a different disease to identify the largest number of tested patients who carry one or more selected tested abnormal gene sites relative to all the tested patients for each site tested in a predefined segment of the world wide population, comprising the steps of:

providing a list ordered from the most frequently occurring to the least frequently occurring chromosomal anomalies including at least two chromosomal anomalies that result in the different genetic diseases, wherein the different genetic diseases are being derived from the list beginning with the most frequently occurring chromosomal anomaly in the predefined segment of the world wide population;

selecting a threshold of the chromosomal anomaly occurrence with respect to the predefined segment of the world wide population;

selecting the at least two chromosomal anomalies for testing when the frequency of occurrence of the chromosomal anomaly and gene mutation in the predefined segment of the world wide population exceeds the threshold;

providing a sample of DNA for testing; and, simultaneously testing the sample for the presence of the selected at least two chromosomal anomalies.

Another object of the present invention is to provide a method of simultaneously testing for a plurality of sets of chromosomal anomalies, wherein the step providing a list ordered from the most frequently occurring to the least frequently occurring chromosomal anomalies and gene mutations comprises:

formulating a multiplicative product of the frequency of occurrence of the genetic disease in the predefined segment of the world wide population times the proportion of the total number of chromosomal abnormalities and gene mutations tested in the selected gene site.

Another object of the present invention is to provide a method of simultaneously testing for a plurality of sets of chromosomal anomalies, wherein the step of simultaneously testing the sample for the presence of the selected at least two chromosomal anomalies, further comprises the step of:

simultaneously testing the sample for the presence of the selected at least twenty chromosomal anomalies.

Another object of the present invention is to provide a method of simultaneously testing for a plurality of sets of chromosomal anomalies, wherein the step of simultaneously testing the sample for the presence of the selected at least two chromosomal anomalies, further comprises the step of:

simultaneously testing the sample for the presence of the selected at least thirty chromosomal anomalies.

Another object of the present invention is to provide a method of simultaneously testing for a plurality of sets of chromosomal anomalies, wherein the step of simultaneously testing the sample for the presence of the selected at least two chromosomal anomalies, further comprises the step of:

simultaneously testing the sample for the presence of the selected at least thirty-seven chromosomal anomalies.

Another object of the present invention is to provide a method of simultaneously testing for a plurality of sets of chromosomal anomalies, wherein the step of simultaneously testing the sample for the presence of the selected at least two chromosomal anomalies, further comprises the step of:

simultaneously testing the sample for the presence of the selected at least three chromosomal anomalies.

Another object of the present invention is to provide a method of simultaneously testing for a plurality of sets of chromosomal anomalies, wherein the step of simultaneously testing the sample for the presence of the selected at least two chromosomal anomalies, further comprises the step of:

simultaneously testing the sample for the presence of the selected at least six chromosomal anomalies.

Another object of the present invention is to provide a method of simultaneously testing for a plurality of sets of chromosomal anomalies, wherein the at least two chromosomal anomalies are unrelated.

Another object of the present invention is to provide a method of simultaneously testing for a plurality of sets of chromosomal anomalies, wherein each of the chromosomal anomalies in the list cause genetic disease for the predefined segment of the world wide population.

Another object of the present invention is to provide a method of simultaneously testing for a plurality of sets of chromosomal anomalies, wherein the step of simultaneously testing the sample for the presence of the selected at least two chromosomal anomalies, further comprises the step of:

simultaneously testing the sample for the presence of the selected at least three chromosomal anomalies.

Another object of the present invention is to provide a method of simultaneously testing for a plurality of sets of chromosomal anomalies, wherein the step of simultaneously testing the sample for the presence of the selected at least two chromosomal anomalies, further comprises the step of:

simultaneously testing the sample for the presence of the selected at least six chromosomal anomalies.

DEFINITIONS

To aid in understanding the invention, several terms are defined below.

"PCR amplification reaction mixture" refers to an aqueous solution comprising the various reagents used to amplify a target nucleic acid. These include: enzymes, aqueous buffers, salts, target nucleic acid, and deoxyribonucleoside triphosphates. Depending upon the context, the mixture can be either a complete or incomplete amplification reaction mixture and the primers may be a single pair or nested primer pairs.

"PCR amplification reagents" refer to the various buffers, enzymes, primers, deoxyribonucleoside triphosphates (both conventional and unconventional), and primers used to perform the selected amplification procedure.

"Amplifying" or "Amplification", which typically refers to an "exponential" increase in target nucleic acid, is being used herein to describe both linear and exponential increases in the numbers of a select target sequence of nucleic acid.

"Bind(s) substantially" refers to complementary hybridization between an oligonucleotide and a target sequence and embraces minor mismatches that can be accommodated by reducing the stringency of the hybridization media to achieve the desired priming for the PCR polymerases or detection of hybridization signal.

The phrase "biologically pure" refers to material that is substantially or essentially free from components which normally accompany it as found in its native state. For instance, affinity purified antibodies or monoclonal antibodies exist in a biologically purified state.

As used to refer to nucleic acid sequences, the term "homologous" indicates that two or more nucleotide sequences share a majority of their sequence. Generally, this will be at least about 70% of their sequence and preferably at least 95% of their sequence. Another indication that sequences are substantially homologous is if they hybridize to the same nucleotide sequence under stringent conditions (see, e.g., Sambrook et al., Molecular Cloning—A Laboratory Manual, Cold Spring Harbor Laboratory, Cold Spring Harbor, N.Y., 1985). Stringent conditions are sequence-dependent and will be different in different circumstances. Generally, stringent conditions are selected to be about 5 degrees C. lower than the thermal melting temperature (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60 degrees C.

As used to refer to proteins or polypeptides, the term "homologous" is meant to indicate two proteins or polypeptides share a majority of their amino acid sequences. Generally, this will be greater than 90% and usually more than 95%.

"Hybridizing" refers to the binding of two single stranded nucleic acids via complementary base pairing.

"Nucleic acid" refers to a deoxyribonucleotide or ribonucleotide polymer in either single- or double-stranded form, that unless otherwise limited also encompass known analogs of natural nucleotides that can finction in a similar manner as naturally occurring nucleotides.

"Nucleotide polymerases" refers to enzymes able to catalyze the synthesis of DNA or RNA from a template strand using nucleoside triphosphate precursors. In the amplification reactions of this invention, the polymerases are template-dependent and typically add nucleotides to the 3'-end of the polymer being synthesized. It is most preferred that the polymerase is thermostable as described in U.S. Pat. No. 4,889,819, incorporated herein by reference.

The term "oligonucleotide" refers to a molecule comprised of two or more deoxyribonucleotides or ribonucleotides, including primers, probes, nucleic acid fragments to be detected, and nucleic acid controls. The exact size of an oligonucleotide depends on many factors including its ultimate function or use. Oligonucleotides can be prepared by any suitable method, including, cloning and restriction enzyme digestion of appropriate sequences and direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method ofBeaucage et al., 1981, Tetrahedron Lett. 22:1859-1862; and the solid support method of U.S. Pat. No. 4,458,066, each of which is incorporated herein by reference.

The term "primer" refers to an oligonucleotide, whether natural or synthetic, capable of acting as a point of initiation of DNA synthesis under conditions in which synthesis of a primer extension product homologous to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends upon its intended use but typically ranges from 15 to 70 nucleotides. Short primer molecules generally require cooler temperatures to form sufficiently stable hybrid complexes with the template. A primer need not reflect the exact sequence of the template but must be sufficiently complementary to hybridize to a template.

The term "primer" may refer to more than one primer, particularly in the case where there is some ambiguity in the information regarding one or both ends of the target region to be amplified. For instance, if a region shows significant levels ofpolymorphism or mutation in a population, mixtures of primers can be prepared that will amplify alternate sequences. A primer can be labeled, if desired, by incorporating a label detectable by spectroscopic, photochemical, biochemical, immunochemical, or chemical means. For example, useful labels include p32, fluorescent dyes, electron-dense reagents, enzymes (as commonly used in an ELISA), biotin, or haptens and proteins for which secondary labeled antisera or monoclonal antibodies are available. A label can also be used to "capture" the primer, so as to facilitate the immobilization of either the primer or a primer extension product, such as amplified DNA on a solid support.

"Probe" refers to an oligonucleotide which binds through complementary base pairing to all or part of a target nucleic acid. It will be understood by one of skill in the art that probes will typically substantially bind target sequences lacking complete complementarity with the probe sequence depending upon the stringency of the hybridization conditions. The probes are preferably directly labeled as with isotopes or indirectly labeled such as with biotin to which an avidin or streptavidin complex may bind later. By assaying for the presence or absence of the probe, one can detect the presence or absence of the target.

"Recombinant" when referring to a nucleic acid probe indicates an oligonucleotide that is free of native proteins and nucleic acid typically associated with probes isolated from the cell, which naturally contains the probe sequence as a part of its native genome. Recombinant probes include those made by amplification such as PCR and genetic cloning methods where bacteria are transformed or infected with the recombinant probe.

The term "reverse transcriptase" refers to an enzyme that catalyses the polymerization of deoxynucleoside triphosphates to form primer extension products that are complementary to a ribonucleic acid template. The enzyme initiates synthesis at the 3'-end of the primer and proceeds toward the 5'-end of the template until synthesis terminates. Examples of suitable polymerizing agents that convert the RNA target sequence into a complementary, DNA (cDNA) sequence are avian myeloblastosis virus reverse transcriptase and *Thermus thermophilus* DNA polymerase, a thermostable DNA polymerase with reverse transcriptase activity marketed by Perkin Elmer Cetus, Inc.

As used herein, the term "sample" refers to a collection of biological material from an organism containing nucleated cells. This biological material may be solid tissue as from a fresh or preserved organ or tissue sample or biopsy; blood or any blood constituents; bodily fluids such as amniotic fluid, peritoneal fluid, or interstitial fluid; cells from any time in gestation including an unfertilized ovum or fertilized embryo, preimplantation blastocysts, or any other sample with intact interphase nuclei or metaphase cells no matter what ploidy (how many chromosomes are present). The "sample" may contain compounds which are not naturally intermixed with the biological material such as preservatives anticoagulants, buffers, fixatives, nutrients, antibiotics, or the like.

The terms "allele-specific oligonucleotide" and "ASO" refers to oligonucleotides that have a sequence, called a "hybridizing region," exactly complementary to the sequence to be detected, typically sequences characteristic of a particular allele or variant, which under "sequence-specific, stringent hybridization conditions" will hybridize only to that exact complementary target sequence. Relaxing the stringency of the hybridizing conditions will allow sequence mismatches to be tolerated; the degree of mismatch tolerated can be controlled by suitable adjustment of the hybridization conditions. Depending on the sequences being analyzed, one or more allele-specific oligonucleotides may be employed. The terms "probe" and "ASO probe" are used interchangeably with ASO.

A "sequence specific to" a particular target nucleic acid sequence is a sequence unique to the isolate, that is, not shared by other previously characterized isolates. A probe containing a subsequence complementary to a sequence specific to a target nucleic acid sequence will typically not hybridize to the corresponding portion of the genome of other isolates under stringent conditions (e.g., washing the solid support in 2×SSC, 0.1% SDS at 70 degrees C.).

"Subsequence" refers to a sequence of nucleic acids that comprise a part of a longer sequence of nucleic acids.

The term "target region" refers to a region of a nucleic acid to be analyzed and may include polymorphic or mutation sites.

The term "thermostable polymerase enzyme" refers to an enzyme that is relatively stable when heated and catalyzes the polymerization of nucleoside triphosphates to form primer extension products that are complementary to one of the nucleic acid strands of the target sequence. The enzyme initiates synthesis at the 3'-end of the primer and proceeds toward the 5'-end of the template until synthesis terminates. A purified thermostable polymerase enzyme is described more fully in U.S. Pat. No. 4,889,818, incorporated herein by reference, and is commercially available from Perkin-Elmer Cetus Instruments (Norwalk, Conn.). thermostable polymerase" typically can resist repeated heating to remain active through multiple DNA denaturation cycles.

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 1E shows tetraploid cells have four copies of each allelic target (4), twice the normal number of sequences inherited from each parent. Tetraploidy in this illustrated conceptus' DNA resulted from fertilization of one ovum by three sperm. The left group shows that of the three alleles inherited from the father and one from the mother, two paternal alleles (2) were of the first (left) allelic length; one longer allele from either parent is reflected by the central peak (1), and one still longer allele from the other parent is represented by the right peak. The second from left group shows that of the three alleles inherited from the father and one from the mother, two alleles are the first length (2) and two alleles are a second length (2). The third from left group shows that of the three alleles inherited from the father and one from the mother, three alleles are of the first length (3) and one allele is a second length (1). The right peak shows that of the three alleles inherited from the father and one from the mother, all are of the same length (4).

FIG. 1F shows tetraploid cells may arise by failure of diploid cells to divide following conception. In this instance, the two groups on the left are observed in the chromosomes inherited from both parents and in the sex chromosomes illustrated on the right. The left group shows that of the replicated single allele inherited from the father and single allele inherited from the mother, two paternal allelic equivalents (2) and two maternal allelic equivalents (2) are observed. The second from left group shows that of the two alleles inherited from the father and two from the mother, all are of the same length (2+2=4). The third from left group shows a typical result of a male cell in which the male determining gene on the Y chromosome (SRY) is found in two copies found in a peak with twice the volume of one allele because the single original diploid SRY gene in this male cell was replicated. Furthermore, two copies of a maternal sequence on the X chromosome of a longer length are found with it in a peak with twice the volume of one allele (X). The right peak shows that one single allele inherited from the father on the X chromosome and other single allele from the mother on the X chromosome in the conceptus' diploid cell are all the same length and doubled in number to a total of four as reflected by the area under the peak $\{[(1+1)\times 2]=4\}$.

FIG. 1G shows a triploid conceptus has 69 chromosomes instead of the normal 46 chromosomes, two from one parent and one from the other parent. Thus most chromosomal regions will have three target copies that may be the same or different length PCR amplified fragments. The left shows three different alleles each of equal copy number at the first tested site. The second from left group shows two identical length sites and one different length site each of equal copy number (2:1) at the second site tested. The right peak shows three identical length alleles each with equal copy numbers at the third site tested.

DESCRIPTION OF A PREFERRED EMBODIMENT

Figure 1A:
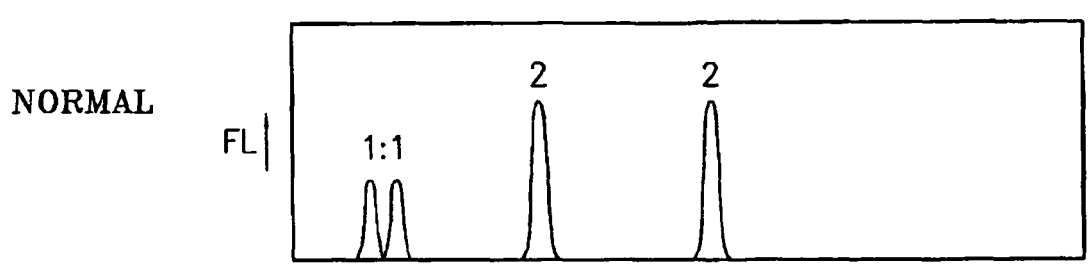
FIG. 1A shows normal DNA with two different length alleles of equal copy number (labeled 1:1) at the first site tested (far left) and two alleles of the same length (2 and 2) at both the second and third sites tested.

Described herein are methods to optimally construct nucleic acid kits to test for target copy number of the selected gene regions in the designated chromosome bands and in common genetic disease genes as well as common gene mutations in common genetic disease genes that together are required for normal growth and development. When genes in these banded chromosome regions are abnormal in number or sequence, viable abnormal fetuses may live to term and beyond.

Some day every child born in the United States will have its DNA extracted and screened from cord blood for the most common genetic disease mutations. Another screen will exist for pregnant mothers seeking prenatal care, and a third will be used once to test aging citizens to optimize their lifelong medical care. The panel of tested mutations for each category will depend upon the part of the world from which the patient's ancestors came. For instance, if the technical issues can be addressed with the microchip, 1000 to 8000 mutations will be tested simultaneously on a single microchip. Specific microchips will be constructed and applied specifically to patients with ancestors from Northern Europe, the Mediterranean, the Middle East, Africa, Southeast Asia, or the rest of Asia. In this fashion a substantial proportion of selected disease genes will be detected in affected patients or those with a single detectable autosomal recessive allele. These people and their families can then be thoroughly tested at the same genetic disease locus for another abnormal allele.

Because a significant proportion of hospitalized children have a human genetic disease, a major contribution to optimize maternal and child health would be to construct and update a prioritized list of genetic disease genes with the common mutations to be tested in newborns or prenatally in mothers or their fetuses. This list would be prioritized according to (1) the most common mutations and the proportion of affected individuals that have these alleles, (2) the reported or estimated disease frequency, (3) whether the disease is found worldwide or is more prevalent in one race or ethnic group, and (4) which diseases could be prevented or treated. These disease lists would be available for comment and modification via the worldwide web to all physicians, scientific investigators, testing laboratories, oversight committees, insurance companies, and government officials who optimize our health care dollars and address important ethical issues.

Given the existence of this list, the Genetic Services Branch in the maternal and Child Health Bureau can organize the most optimal DNA newborn population genetic screening program. For instance, a Mass spec might test 100 multiplexed sites and a microchip test 1000 sites per sample. Either of these formats can simply proceed down the list and add the highest priority mutations required to develop the most comprehensive test with the highest rate of abnormal pickup to optimally utilize the available testing format. Whether one or both formats are available, selecting a population screening method requires considering the cost, the detection rate of the test, and the reliability and turn around time of the test method. Having a readily available list of common diseases and their common mutations will make this process straightforward and much more effective in determining the relative efficacy of different tests that could be compared according to the same rational standard. Additional lists will be constructed for major populations throughout the world so that an optimum test panel exists for each person. These lists will also serve as the basis for developing tests for pregnant mothers and older citizens. With public funds supporting this effort and dissemination via the worldwide web, greater access to oversight agencies will allow for a more comprehensive review of the ethical issues than by laboratories developing the tests that must be more focused on the cost of each test.

At the same time, the information used to make these decisions is changing as new disease genes are being identified. For instance, Rett syndrome (RTT) is a common and important genetic disease that affects about 1 in 12,000 girls (Rett, 1966; Hagberg et al, 1983, 1997) and accounts for approximately 10% of profoundly handicapped females (Hampson et al, 2000). Rett syndrome results from mutations in the MECP2 gene on the X chromosome (Amir et al, 1999). In developing a test for all Rett syndrome patients, a hotspot of gene deletions was found and the inventors developed a test for the five mutations that result in half of all the Rett syndrome mutations (Lebo et al, Clinical Genetics, In Press; Milunsky et al, Am. Soc. Pediatrics Mtg., 2001). These common mutations from the publications were derived by six groups that found Rett gene mutations in 120 patients (Amir et al, 1999; Wan et al, 1999; Huppke et al, 2000; Obata et al, 2000; Hampson et al, 2000; Bienvenu et al, 2000; FIG. 1A). Similar information can be obtained for other genetic diseases with access to references that can be purchased and downloaded directly through PubMed and a local Medical School library. These must then be studied, the information collated and the frequencies of individual mutations calculated. The five most common Rett syndrome mutations would most likely be included in a 1000 mutation test screen and might be included in a 100 mutation test screen. With the recent completion of the Human Genome Project, it can be expected that many genetic disease loci will be identified and characterized quickly.

The primary challenge in compiling lists of genetic disease mutations to be screened in different age groups is to obtain sufficient resources to obtain and review all available literature and have a geneticist review and calculate the relative proportion of affected individuals that would be detected.

Previously the PI reported a list of DNA tests that at the time were considered to be sufficiently robust to be used in clinical testing based upon the percent of informative patients and the percent reliability of the result used to make clinical decisions (Lebo et al, Am J Hum Genet 47:583-590, 1990). The PI maintained the list until it grew to three times the length when the project became too large to accommodate with the available resources. The current number of diseases that might be added to this list has grown over 20-fold A list of diseases in order of prevalence and the frequency of the most common alleles would be even more useful today because technical advances now provide the means to develop a multiple genetic disease screening test.

The PI has also developed or optimized multiple prenatal and preimplantation tests in molecular genetics and molecular cytogenetics. For instance, he holds patents on Charcot-MarieTooth Type 1B molecular testing (Lebo et al, 1991a, 1991b; Su et al, 1993; Lebo and Ravetch, Lebo R V, Ravetch J V: U.S. Pat. Nos. 5,876,927 and 5,723,593) and on FISH deletion analyses of diseases like steroid sulfatase deficiency, Duchene muscular dystrophy, retinoblastoma, and CMTIA (Lebo et. al., 1993; Lebo: U.S. Pat. No. 5,665,540). His laboratory also used a mouse model of CMTIB and one of CMTIA to demonstrate that preimplantation diagnosis can be completed with a reliability of 97% and >99% respectively (Kim et al, 1999; Sago et al, 1997). The PI developed six prenatal DNA diagnostic tests including aneuploid chromosome 13, 18, 21, X and Y analysis of direct amniocytes (Lebo et al, 1992; Lapidot-Lifson, 1995), a McArdle disease test (Lebo et al, 1990), and a prenatal human sex determining SRY gene test. His laboratory also reported unusual cases encountered in the prenatal diagnosis of Duchene Muscular Dystrophy.

Currently projects throughout the nation are developing new technologies to do mass screening. Ongoing development of a cystic fibrosis test with a goal of 100 mutations screened by mass spectrometry is being funded. Currently over half are being screened in Roger Lebo's previous clinical laboratory under the direction of Zhenyuan Wang, PhD. Furthermore, Farid Chehab, Ph.D. is developing microchip analysis of cystic fibrosis mutations at the University of California San Francisco. As these technologies become more routine, additional genetic disease loci can be tested according to the priorities defined by the proposed study.

For instance, cystic fibrosis results in about 1 in 2500 affected newborns in the Caucasian population or about 400 affected patients among 1,000,000 Caucasian newborns. Testing 45 mutations detects approximately 89% of the mutations in the northern European population. This would characterize both mutations in 317 cystic fibrosis patients and one mutation in 78 patients who could be determined to have cystic fibrosis by a subsequent sweat test. No mutations would be detected in 5 cystic fibrosis patients. Testing an additional 45 cystic fibrosis mutations for a total of 90 mutations adds no more than 1% additional detected alleles (assume a total of 90% detected). Thus testing 90 cystic fibrosis mutations in 1,000,000 Caucasian newborns would find 2 mutations in 325 newborns, one mutation in 72 newborns, and no mutations in 4 cystic fibrosis patients. Therefore cystic fibrosis would not be suspected in 5 newborns after testing 45 mutations and 4 newborns after testing 90 mutations in 1,000, 000 newborns. In contrast, by testing 12 sites in the dystrophin gene that results in Duchenne muscular dystrophy in males, one would detect the 70% of the males carrying a partial gene deletion. Since the frequency of DMD is 1 in 5,000 male newborns or 1 in 10,000 newborns, testing 12 DMD gene sites in 1,000,000 fetuses or 500,000 male newborns would detect 70 males with Duchenne muscular dystrophy. Therefore one could conclude that a screening test for cystic fibrosis should not continue beyond 45 mutations and that a screen for Duchenne muscular dystrophy at 12 sites should also be added if a test with 90 mutations were made available. This is a simplified, non-limiting, example. In fact, nearly all DMD deletions are detected by testing six locations and substantially fewer cystic fibrosis Conducting a DNA test that identifies more fetal abnormalities than Giemsa-banded karyotyping requires searching the entire genome for important chromosome regions that when abnormal result in viable newborns. The most readily apparent abnormalities involve differences in the number of whole chromosomes or chromosome regions that result when one of a very large majority of chromosome rearrangements occurs. Therefore quantification of the relative number of target sequences is required to distinguish the normal autosomal and pseudoautosomal diploid two copies from haploid, male sex chromosome copies and all other abnormal copy number in every cell: 0, 1, 3, 4, >4. Mosaic copy number when detected is also of importance in symptomatic patients with abnormal chromosome rearrangements and very important in oncology patients.

Therefore DNA analysis must not only identify but quantify the number of target alleles at any single site selected for analysis. The most reliable method is to be selected to determine gene copy number. Several methods have been used to quantify target genes: (1) restriction enzyme analysis to give known length restriction fragments for each allelic type (Lebo et al., 1990), fluorescence in situ hybridization to interphase nuclei or metaphase chromosomes to detect gene deletion (Lebo et al, 1993a) or duplication (Lebo et al., 1993b), quantitative PCR (QPCR; Mansfield, 1992), comparative genomic hybridization to metaphase chromosomes or nucleic acid arrays (Pinkel et al, 1998), and Invader technology (Third Wave Technologies) with 4 colors on one spot. The reliability of any quantification method can be optimized by adding more colors, more independent assays, and more normal and abnormal controls. Furthermore, while interlocus comparison has been sufficiently reliable for QPCR analysis (Mansfield, 1992), testing distinguishable polyorphic alleles simultaneously will further enhance reliability as the same flanking sequences are being tested simultaneously. No matter the method selected, the final result must be highly reliable and reflex tests must be easy and rapid because a single reflex test doubles the assay time. On the order of 50 tests are the minimal number required to offer a robust genetic test with high pickup rate of genetic abnormalities in prenatal samples. This number will vary depending upon the age of the patient tested, the number of appropriate tests, and whether the tested tissue is derived from a suspected or known neoplastic tissue. Of the previously mentioned current protocols, restriction enzyme analysis is too time consuming and in situ hybridization is time and labor intensive, leaving QPCR, CGH, and Invader.

The well characterized categories of chromosome abnormalities and their relative frequencies in newborns has been reported (refer to Lebo et al, 1992, Table III). The relative numbers of phenotypic abnormalities involving rearrangements other than abnormal chomosome number was divided into high risk (>10% of anatomic malformations and anatomic delay), and Low Risk (5-10% risk). Given that 2% of fetuses in the high risk group have unbalanced translocations, then an estimated 97% of these abnormalities would be detected by testing 26 chromosome sites: 1q, 2p, 2q, 3p, 4p, 5p, 5q, 6q, 7p, 8p, 8q, 9p, 10p, 10q, 11q, 12p, 14q, 15q, 16p, 17q, 18p, 18q, 19q, 20p, 21q, and 22q (Table 1). [Note: This 97% is estimated by assuming the values like <1.3 for lqter (q23-32) is =1.3 and that recombination occurs equally in the distal arms of different chromosomes.] Although some deletions will be tested by quantification of these 26 chromosome sites, the 1% of deletions with high risk of abnormality were calculated from Table III as though all were missed. In the LOW risk category III In Table III, the risk of abnormality is 7% of all chromosome abnormalities and the likelihood of anatomic malformation or developmental delay is 5-10%.

Because this category of chromosome abnormalities would have been missed completely, we calculated the likelihood of not detecting these abnormalities as 7%×7.5%=0.525%. The marker and insertion chromosomes have been combined in Table III because these categories were combined when merging the data by Vogel and Motulsky (1986) and Nielsen and Sillisen (1975). Assuming that each category contributes to half of the 11%, then 5.5% of insertions will have about a 7.5% risk of abnormality [5/5%×7.5%=0.4125%. Furthermore, half of a series of 50 marker chromosomes were dup (15) and 12% were iso(12p) and iso(18p). Thus These abnormalities would be detected by the SNRPN gene probes used to test Prader-Willi deletions and the 12p and 18p loci tested in the above list used to search for unbalanced translocations: [5.5%×62%×7.5%=0.255%]. Therefore the total percent of abnormal chromosome rearrangements detected by quantification of 27 loci (26 above plus the 1 SNRPN gene, Table 1) would be 1.94%. Overall, this test would pick up 518 newborns with phenotypically abnormal chromosome rearrangements in 100,000 newborns and miss 13.

In contrast, adding 7 sites in the Duchenne muscular dystrophy gene would detect 5 de novo mutations in 100,000 newborns (Table 1); quantifying the SNRPN gene locus would detect the 70% of deletions in the Prader-Willi and Angelman Syndromes and detect 5 additional de novo mutations in 100,000 newborns, testing the PMP22 gene copy number would detect the 4 de novo CMT1A mutations and any HNPP mutations, testing the ELN gene site would detect the 10 Williams syndrome newborns, while testing the SRY gene site and the AZF gene on Yq11.2 would determine sex and detect females with a high risk for gonadal cancer and a portion of azoospermic males. Excluding the Y chromosome loci, these additional 11 sites (added to 27 above, Total=38) would determine sex and detect 24 additional newborns with a major genetic abnormality (about twice the 13 that were missed in the rare abnormal chromosomal category above).

Additional selective gene sites can be added that were not mentioned like the DiGeorge syndrome critical region on chromosome band 22q11 and other common gene or chromosome deletion syndromes as these are characterized. Furthermore, additional chromosome sites can be characterized selectively as more information is collected. For instance, 8 more sites (3q, 4q, 6p, 7q, 9q, 11p, 13q, and 17p) to pick up the other reported viable unbalanced translocation sites affecting an estimated 3% of the newborns with unbalanced translocations with this entire class of chromosome rearrangements representing 2% of all abnormal chromosome rearrangements (about 1 per 300,000 newborns).

The sites to be tested are all important in development as mutations at these sites result in genetic disease. These tested sites may be modified according to the population to be tested and the additional data gathered about the frequencies of mutations in disease-causing mutant genes in the same chromosome bands, or whether one is screening oncology patients likely to have mutations in oncogenes. Nevertheless, the principle of selecting genetically important sites for directing development of or maintaining normal tissues remains constant.

Some genetic diseases are common in worldwide populations like Rett syndrome with an estimated frequency of 1/10,000 to 1/15,000. As 8 point mutations account for about 66% of all Rett gene mutations, testing for these 8 additional sites (38 above plus 8=46 loci) would detect de novo mutations in 8 fetuses. Together this would detect 32 fetuses with de novo mutations that would not have been tested otherwise.

Depending upon the region of the world from which the patient's ancestors were derived, the screening test would also be optimized for the common genetic disease mutations to be tested. For instance, the sickle cell anemia mutation is common in African blacks, the beta thalassemia mutations are common in the Mediterranean, the alpha and beta-thalassemia mutations are common in Southeast Asia, hemophilia is common in Korea, and cystic fibrosis is common in Caucasians. For instance, testing for the common ΔF508 mutation locus in the cystic fibrosis transmembrane receptor gene (Riordan et al, 1989) will detect 70% of cystic fibrosis mutations in the Caucasian population and will detect at least one mutation in 91% of fetuses affected with cystic fibrosis. Therefore adding this single point mutation test to the other sites tested will detect 31 fetuses or newborns with cystic fibrosis out of 100,000 tested.

Different disease tests should be completed at different stages of the life cycle. Huntington disease testing has been reserved for patients requesting the test who are over 21 years of age. The number of couples requesting prenatal diagnosis are rare because the at-risk parent generally does not want testing prior to developing symptoms, perhaps because no cure is available. In contrast, testing patients is becoming more common for increased risk for pulmonary emboli, colon cancer, breast cancer, or other genetic diseases for which medical interventions exist that are more effective or likely to be applied regularly when the increased risk is known. These tests will become part of panels recommended for patients at different stages of their life cycle.

One method to quantify selected target loci is to do quantitative PCR (QPCR) with internal control sites to determine the number of alleles at each tested site. Quantitative PCR to detect the number of alleles is most effective when highly polymorphic allelic sites are tested and the quantities of two or more different allelic products are compared (Wyandt et al., 2000). In Wyandt et al. the amount of product is determined by densitometry scanning of X-ray film exposed to $P^{32}$-labeled PCR product. Four different alleles instead of two were demonstrated by three peaks, one of which had twice the product as the other two, to give a pattern representing four different alleles. Four allelic targets are unusual. Most sites normally have two alleles, with one allele following deletion and three alleles following duplication. If one target had three copies of alleles of three different lengths, the products would give three different length peaks with equal area under each peak. With three alleles and two different lengths the result would be two different peaks, one of which had twice the area under it as the adjacent peak. With two alleles that were polymorphic either two equal size different length adjacent peaks would be scored or one peak with twice the area under the peak reflecting two alleles. With one allele, a single peak would always appear with an area under the peak reflecting one allele equivalent. Testing the quantity of PCR amplified product for each allele is most readily done when at least two different alleles that can be separated and quantified by the assay exist at the target sequence.

Test Procedure

When testing highly informative polymorphic loci, the frequencies of detecting more than one allele are increased considerably. In order to find polymorphic sites in the region of genetic disease genes, identify the largest sequenced DNA fragment containing the gene. Then search the database for the most highly polymorphic sites in the gene region of interest including in overlapping sequenced DNA fragments. The most highly polymorphic loci in the area would be listed in descending order beginning with the highest heterozygosity index. The heterozygosity index of each polymorphic site indicates the proportion of all normal individuals tested that are anticipated to have two different alleles, one on each chromosome, at the tested locus. At normally diploid loci, $$\text{Het.}=1-[(a1)2+(a2)2+\ldots+(an)2]$$

where Het (heterozygosity index) equals the predicted frequency of individuals with different alleles at this locus based upon the observed allele frequencies for each polymorphic length of alleles a1, a2, . . . an with the original sample series tested. For instance, if the calculated heterozygosity index is 0.8, an estimated 80% of randomly tested normal individuals will have two different length alleles at this location. The most reliable result will be obtained by combining all reported data at each locus. Each laboratory may modify the frequencies used for calculations depending upon the results obtained in a series of patients tested by that laboratory. After the most informative loci are ordered in descending order of heterozygosity indices down to perhaps 0.7 or 0.65, all available cytogenetic locations and or centimorgans from the end of the short arm or from the centromere are added to each locus on the list. Next a sufficient number of loci are chosen to be informative at a preselected frequency to determine whether each tested chromosome region has the normal number of copies or an aneuploid copy number. For instance, testing 4 loci each with a heterozygosity index of 0.8 in the same chromosome region will give at least two loci with two different allelic lengths in 96% of all normal individuals tested.

The criteria for distinguishing normal from aneuploid copy number are anticipated to be different for the different chromosomal loci tested because the frequency of different comparable outcomes will vary according the individual heterozygosity indices at the loci tested and the number of loci tested. Thus an optimal test can be designed according to the ultimate application of the test and the reliability required from the result. Distinguishing trisomy from two copies will give at least two different alleles with a 2:1 ratio in a larger proportion of cases than a diploid chromosome region. At trisomic loci, $$\text{Het.}=1-[(a1)3+(a2)3+\ldots+(an)3]$$

where Het equals the predicted frequency of individuals with three alleles of at least two different sizes at this locus based upon the observed allele frequencies for each polymorphic length of alleles a1, a2, an with the original sample series tested. Therefore a locus with a heterozygosity index of 0.8 in a normal individual will have at least two different length alleles in an estimated 96% of individuals tested with three copies of this locus. Thus the effort required to identify polymorphic sites with the highest heterozygosities in diploid humans is well worth the effort.

In contrast, distinguishing aneuploidy in the sex chromosomes will require testing loci on two different chromosomes X and Y and comparing these results to autosomal and pseudoautosomal control loci. The origin of two or more sex chromosomes is anticipated to give polymorphic site discrimination the same as for two or more autosomes (chromosomes 1 to 22) as described above. In contrast, the presence of 2 or more Y chromosomes in a human fetus is anticipated to come from two identical copies of the Y chromosome from the father. The presence of a single Y chromosome can be detected easily by PCR amplifying the SRY gene and/or the ZFY gene and the amelogenin Y gene. Distinguishing more than 1 Y chromosome copy from 1 Y chromosome copy can be done by comparing the peak height of a unique PCR amplified site with an autosomal site. Further confirmation of more than 1 Y chromosome can also be obtained by comparing the number of PCR amplified sites in the pseudoautosomal regions of the end of the short arms of both the X and Y chromosomes where identity between these chromosome regions is maintained by meiotic recombination.

Determining aneuploidy with a reliability sufficient to terminate a pregnancy will require highly reliable test results. A first round screening test for aneuploidy may require a second round QPCR test to confirm suspicious. Alternatively, a different test method that alone may be less reliable may along with the first test still exceed the reliability of all existing prenatal tests except cytogenetics. Thus a second tier of tests that characterize additional sites in the same chromosome region can be used to retest genomic regions that appear to be abnormal without sufficient corroborating evidence to make an irreversible clinical decision. For instance, terminal deletion of the long arm of chromosome 16 may be evident from two different polymorphic loci that each amplify half as well as the other autosomal loci. Nevertheless, amplification of two or more additional loci in this chromosome region may need to be compared to a coamplified normal chromosome region in order to confirm the diagnosis.

Figure 1B:
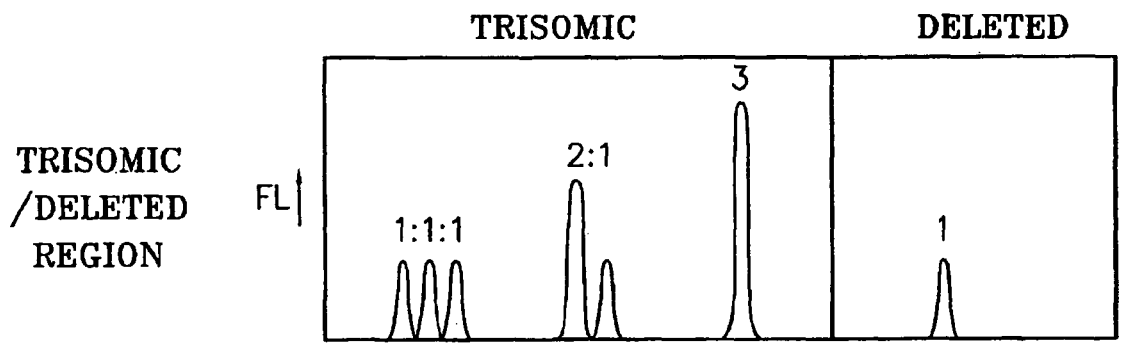
FIG. 1B shows an abnormal patient DNA on the left with three different length target sites each of equal copy number (1:1:1) at the first site tested (far left in left window); two identical length sites and one different length site each of equal copy number (2:1) at the second site tested (second from left); and three identical length sites each of equal copy number (3) at the third tested site (third from left). Three target sites typically indicate one site more than normal. The right side of FIG. 1B shows an abnormal patient DNA result when one (1) allele is present at the only tested locus. One target site typically reflects one site less than normal.
Figure 1C:
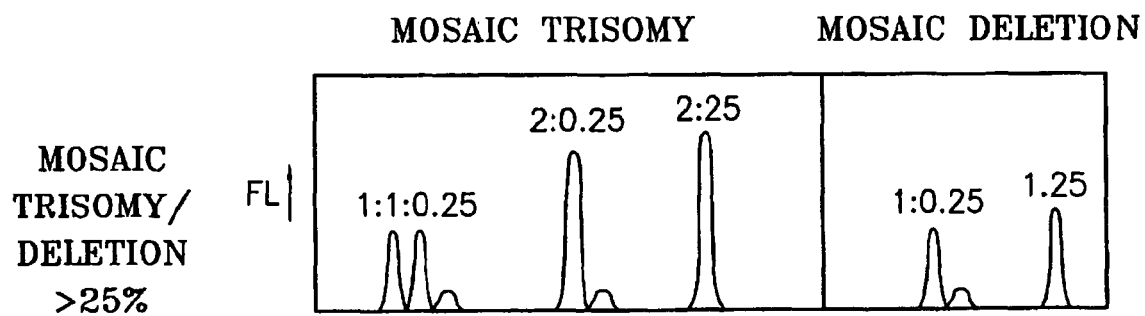
FIG. 1C shows on the left side, a patient with mosaic target copy number abnormality i.e. about 75% having two normal target sites and about 25% of cells have three target sites. The far left in left window shows a patient with three different length target alleles with the left two alleles (1:1) in all cells and the third allele (0.25) in only about 25% of cells. Second from left shows two identical length alleles (2) in all cells and a third different length allele (0.25) in about 25% of cells. Third from left shows identical length alleles in all cells: two identical length alleles in about 75% of cells and three identical length alleles (2.0+0.25=2.25) in about 25% of the remaining cells with an extra copy of the tested chromosome region. The right side of FIG. 1C shows a patient with mosaic cells i.e. most cells (about 75%) with one target site and some cells (about 25%) of cells with two target sites. Far Right in right window shows a patient with two different target alleles of the same length with one allele (1) in all cells and the second allele (0.25) in only about 25% of cells to result in a (1.25) total allelic content. Second from right shows a patient with one target allele in all cells (1) and a second different length allele (0.25) in about 25% of cells.
Figure 1D:
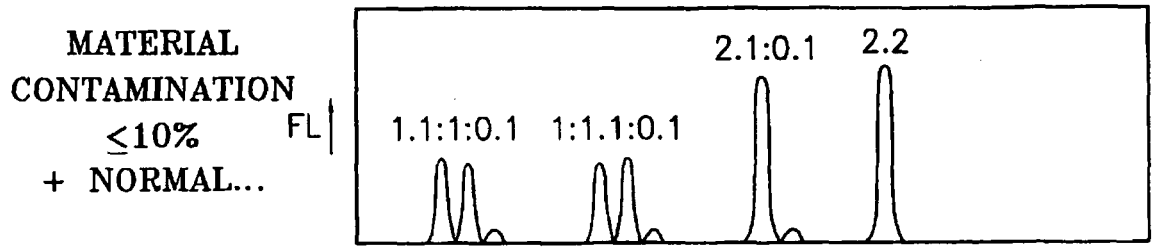
FIG. 1D shows normal fetal cells with one allele inherited from the mother (maternal) and one allele inherited from the father (paternal) contaminated with 10% of maternal cells sampled along with the fetal cells to give peaks of the illustrated ratios. The left side of FIG. 1D shows three different polymorphic allelic peaks. The left peak consists of one fetal allele in all cells and 10% extra copies of the same length allele contributed by the contaminating mother's cells (1+0.1=1.1); the central peak has one copy of the fetal allele in every fetal cell; and the third peak (0.1) has one copy of the different length maternal allele in the maternal cells. Second from left shows three different polymorphic allelic peaks. The left peak has one copy of the fetal allele (1) in every fetal cell; the second peak consists of one fetal allele in each fetal cell and 10% extra copies of the same length allele contributed by the 10% of contaminating mother's cells (1+0.1=1.1); and the third peak (0.1) has one copy of the different length maternal allele only in the maternal cells. The third from left group shows two different polymorphic allelic peaks. The left peak has the two copies of the fetal alleles in every fetal cell and one copy of the different length maternal allele only in the maternal cells (2.1); and the second peak (0.1) has one copy of the different length maternal allele only in the maternal cells. The right group shows one polymorphic allelic peak has the two copies of the fetal alleles in every fetal cell and two copies of the different length maternal alleles only in the 10% of maternal cells (2.0+0.2=2.2).
Figure 1H:
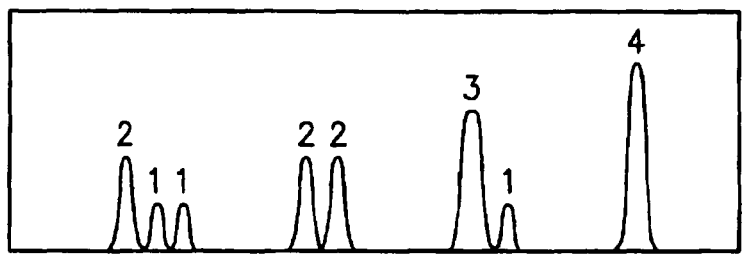
FIG. 1H shows a triploid conceptus resulting from two sperm fertilizing the same egg that results in a 69,XYY karyotype will have sex chromosome patterns illustrated in 1H and autosomalate patterns illustrated in FIG. 1G. The left group shows a single X chromosome site shows one allelic equivalent while two equally amplifying longer Y chromosome sites show two Y chromosome equivalents. The right peak shows three sites in the pseudoautosomal regions shared equally by every X chromosome and Y chromosome will reveal a single peak three times as high as would be found for a single amplified site.
Figure 1H:
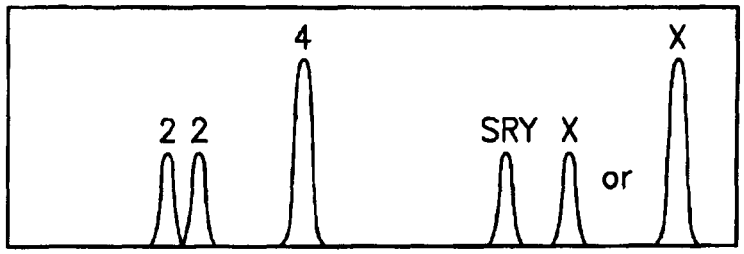
Figure 1H:
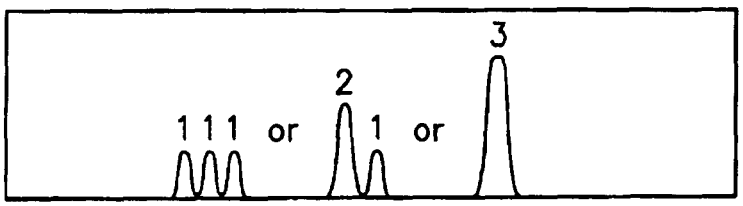
Figure 1H:
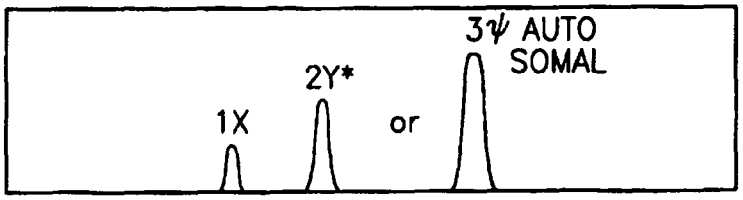

Characterizing the most common chromosome aneuploidies unambiguously is the first priority in prenatal testing because these are the most common chromosome abnormalities. Three other laboratories have reported that testing a very highly polymorphic locus gives three different alleles in a majority of cases of trisomy tested. Still, testing a single chromosome 21 region is anticipated to give at most two different alleles in a substantial proportion of all cases because nondisjunction can occur either in Meiosis I or in Meiosis II. Therefore testing a proximal chromosome locus will usually give only two different parental chromosome arms in about 80% of trisomy 21 fetuses because two identical chromosome regions are passed on by the maternal gamete. However, because recombination occurs in each chromosome pair at meiosis to prevent nondisjunction in most meioses, the distal chromosome region will have two different parental chromosome regions passed on by the same gamete in these same cases. Therefore testing distal chromosome regions in abnormal embryos that resulted from nondisjunction in Meiosis I will detect three different regions and three different alleles at a proportion of the distal highly polymorphic loci tested. If nondisjunction occurs at Meiosis II, the proximal chromosomal loci will be likely to give three different loci and the distal loci will only two different loci. Therefore these two sets of polymorphic loci can be tested for the 5 most common chromosome aneuploidies, loci near the centromere, and more distal loci on the long arm of each chromosome. When testing a sufficient number of proximal and distal loci, three unique peaks will be observed at one of these loci in nearly every case of trisomy (FIG. 1B). Furthermore, if only two peaks are observed that have been amplified from a trisomic region, a two-fold difference in these peaks (FIG. 1B) at multiple loci is also anticipated to be sufficiently reliable to establish a diagnosis.

After the minimum number of polymorphic loci are selected according to the heterozygosity frequencies and chromosome location in order to obtain a DNA result that is sufficiently reliable, the published PCR amplified primer lengths are then compared at all selected loci so that as many different polymorphic sites can be tested simultaneously as possible with no overlap in allelic fragment lengths. Three to four polymorphic sites can generally be amplified by multiplex PCR in the same tube and incorporated with the same color fluorescent label. These can all be analyzed simultaneously in the same lane of an electrophoresis apparatus that records and quantifies each allelic product like those from Applied Biosystems with four different colors and from Lycor with two different colors. If too many polymorphic sites have the same size range allelic products, new primers can be selected from the surrounding genomic sequence until sufficient additional sites have been multiplexed. These might be obtained from the PCR amplified sequence in the database, from the larger site sequence also in the database, or by using additional laboratory protocols published in standard references.

Three different length alleles at any one site will clearly distinguish trisomy unambiguously. Quantifying two different length polymorphic alleles for two equally amplified products of for products with approximately a two-fold difference in product will be tested on multiple samples. More loci will need to be tested if only three different allelic peaks are considered to give unambiguous results (Not shown). This approach is anticipated to distinguish mosaic aneuploid locations from maternal contamination, triploidy, and tetraploidy (FIG. 1, C-G). QPCR is anticipated to represent a substantial improvement over interphase whole chromosome in situ hybridization analysis because multiple informative polymorphic amplified allelic sites are anticipated to confirm all test results. When sufficient reliability has not been achieved for any single chromosome location, a backup test to obtain additional polymorphic information from the same chromosome region can be used.

In partial aneuploidy described as Category 2, the aneuploid chromosome regions reported in phenotypically abnormal surviving patients will be tested along with the whole chromosomes that are most frequently aneuploid (Table 4-3, Gardner & Sutherland, 2nd ed, pp. 87-88, 1996.) Additional chromosome regions will be tested to identify marker chromosomes. The number of chromosome regions tested will be increased to characterize the number of aneuploidies desired.

Deletions account for a majority of mutations in about a dozen genetic diseases. Deletion can be distinguished because only 1 allele or target is amplified instead of the usual 2 on autosomes of normal people. This single allelic product can be compared to the multiple other autosomal target products in the same lane of the gel that resolves each PCR product by size. Polymorphic sites are unnecessary, but multiple sites will probably have to be compared to confirm that only 50% of the usual PCR product has been amplified. Therefore no limitation exists as to the number of target sites that can be amplified because none of the targets need to be polymorphic.

In contrast, single gene duplications like the CMT1A gene locus spanning 0.5 to 1.5 Mb of chromosomal target are anticipated to have between 3 and 8 di-, tri-, or tetranucleotide repeat polymorphic sites. Since few of these sites have heterozygosity indices exceeding 0.7, it is anticipated that insufficient data could be obtained upon which to base an irreversible clinical decision. If testing these sites becomes important, additional approaches may need to be added like sequencing sites with single base pair polymorphisms and comparing the relative quantity of alleles amplified from each DNA sample.

Other approaches to quantity PCR products include hybridizing a PCR amplified cocktail to an array of ASO targets bound to a multitargeted microchip and comparing the fluorescence of each microchip address, and quantifying the amount of PCR product at multiple PCR cycles to compare amplification during logarithmic accumulation. Any of these approaches are going to give more reliable results when testing multiple loci. At the time of writing, the most straightforward means to quantify fluorescent products is by gel electrophoresis that records the quantity of each polynucleotide repeat product with a resolution of 1 basepair intervals.

TABLE 1

Genetic Disease Loci In Critical Chromosome Regions

| Chromosome Band Tested | Gene | Disease Locus Tested | Disease Frequency | OMIM # |
|---|---|---|---|---|
| 1p36.3 | MTHFR | Homocystinuria due to MTHFR deficiency | | 236250 607093 |
| 1q44 | CIASI | FCAS Muckle-Wells Syndrome CINCA Syndrome | N.A. | 606416 |
| 2p25 | TPO | Thyroid Peroxidase Deficiency | N.A. | 274500 |
| 2q37 N.A. | UGT1A1 | Crigler-Najjar Syndrome, Type II Gilbert Syndrome | N.A. | 606785 |
| 3p25-p26 | VHL | Von Hippel-Lindau Syndrome | N.A. | 193300 |
| 3q27 or | TP63 | Tumor Protein P63 | N.A | 603273 |
| 3q28 | LPP | Lipoma-Preferred Partner | N.A. | 600700 |
| 4p16.3 or | FGFR3 | Achondroplasia Huntington | 1/20,000 | 100800 |
| 4p16.3 | HD | Disease | | 143100 |
| 4q35 | FSHMD1A | Facioscapulohumeral muscular dystrophy | 1/250,000 | 158900 |
| 5p15.2-15.3 | MSR | Methionine Synthase Reductase | N.A. | 602568 |
| 5q35.3 or | FLT4 | FMS-Like Tyrosine Kinase | N.A. | 136352 |
| 5q35.2-35.3 | FLT4 | Ehlers-Danlos Syndrome | N.A. | 604327 |
| 6p25 or | FOXC1 | Iridogoniodysgenesis Factor | N.A. | 601090 |
| 6p25-p24 | F13A1 | 13 coagulation enzyme | N.A. | 134570 |
| 6q27 | TBP | Spinocerebellar ataxia 17 | N.A. | 600075 |
| 7p22 | MAD1L1 | Somatic lymphoma | N.A. | 602686 |
| 7q11.2 | ELN | Williams Syndrome | 1/10,000 | 194050 130160 |
| 7q36 | PRKAG2 | Wolff-Parkinson-White Syndrome | N.A. | 602743 |
| 8p23 or | MCPH1 | Microcephaly, autosomal recessive 1 | N.A. | 607117 |
| 8p22 | LPL | Hyperlipoproteinemia I | 1/10,000 | 238600 |
| 8q24.3 | ZIP4 | Acrodermatitis enteropathica | N.A. | 607059 |
| 9p24.2 | PDCD1 | Mouse model develops lupus* | N.A. | 605724 |
| 9q34.3 | AGPAT2 | Berardinelli-Seip Congenital Lipodystrophy 1 | N.A. | 603100 |
| 10p15 | GATA3 | Hypoparathyroidism, sensorineural | N.A. | 131320 |
| 10q26 | OAT | Ornithine Aminotransferase deficiency | N.A. | 258870 |
| 11p15.5 | CDKNC1 | Beckwith-Wiedemann Syndrome | N.A. | 600856 |
| 11q24 | KCNJ1 | Bartter Syndrome, Type 2 | N.A. | 600359 |
| 12p13.3 | VWD | Von Willebrand Factor Deficiency | 1/20,000 | 193400 |
| 12q24.2 | TCF1 | Diabetes Mellitus Transcription Factor 1 | high | 142410 |
| 13q34 | IRS2 | Diabetes Mellitus Insulin receptor substrate | | 600797 |
| 14q32.33 | IGHM | Agammaglobulinemia | N.A. | 147020 |
| 15q11.2 | SNRPN # | Prader-Willi Syndrome | 1/15,000 | 176270 |
| | UBE3A # | Angelman Syndrome | 1/15,000 | 601623 |
| 15q26.1 | RECQL3 | Bloom Syndrome | N.A. | 604610 |
| 16p13.3 | HBA1 | Alpha Thalassemia | (C) | 141800 41850 |
| 16q24.3 | FANCA | Fanconi Anemia | (D) | 227650 |
| 17p13.3 | LIS1 | Miller-Dieker Syndrome | (E) 90% deletions | 247200 |
| 17p11.2 | PMP22 | CMT1A/HNPP | 1/5,000(F) 20% de novo | 601097 162500 |
| 17q25.3 | HSS | Sanfilippo Mucopolysaccharidosis Type IIIA | (G) | 605270 252900 |
| 18p11.3 | TGIF | Holoprosencephaly | N.A. | 602630 |
| 18q23 | CYB5 | Methemoglobinemia | N.A. | 250790 |
| 19p13.3 | ELA2 | Cyclic Hematopoiesis | N.A. | 130130 |
| 19q13.4 | TNNT1 | Nemaline myopathy | N.A. | 191041 |
| 20p13 | AVP | Diabetes Insipidus Neurohypophyseal Arginine Vasopressin | N.A. | 192340 125700 |
| 21q22.3 | ITGB2 | Leukocyte adhesion deficiency | N.A. | 116920 600065 |
| 22q11 | DGCR | DiGeorge Syndrome | N.A. | 188400 |
| 22q13.3 | DIA1 | Methemoglobinemia Diaphorase Deficiency | N.A. | 250800 |
| Xp22.32 | STS | X-linked ichthyosis | 1/5,000 Deletions: 90% | 308100 |
| Xp22.32-pter | SHOX | Short Stature Homeo Box | N.A. | 604271 312865 |

TABLE 1-continued

Genetic Disease Loci In Critical Chromosome Regions

| Chromosome Band Tested | Gene | Disease Locus Tested | Disease Frequency | OMIM # |
|---|---|---|---|---|
| Xp21.2 | DMD | Duchenne Muscular Dystrophy 65% deletions, 7 sites, 90%, 1/3 new mutations | 1/4,000 | 310200 |
| Xq28 | SLC6A8 | Creatine deficiency syndrome X-linked | | 300352 300036 |
| Yp11.3 | SRY | Sex-determining region Y Godndal dysgenesis, XY type | | 480000 |
| Yq11.2 | USP9Y | Azoospermia | | 400005 |

As a non-limiting example, consider the power of multiple gene testing. According to the current standard-of-care protocol, testing 1,000,000 Northern European Caucasian fetuses for 25 cystic fibrosis mutations would detect two mutations and identify 324 affected fetuses: for Cystic Fibrosis with a carrier frequency of 1/29 and 1 in four conceptions affected for at-risk couples who each carry a mutation, the frequency of affected conceptions is (1/29)2×(1/4)=1/3364 or 1 affected fetus among 3422 conceptuses. Testing 1,000,000 conceptuses for the 25 most common cystic fibrosis mutation sites among the >1,000 total mutations reported will detect

[(1/29)2×(1/4)]×0.9×0.9×1,000,000=240 affected fetuses identified.

In comparison, testing 1,000,000 conceptuses for the 78 most common cystic fibrosis mutation sites among the >1,000 total mutations reported will detect

[(1/29)2×(1/4)]×0.92×0.92×1,000,000=251 affected fetuses.

For Duchenne Muscular Dystrophy (DMD), 1 in 2000 males are affected or 1 in 4,000 conceptuses; 1/3 of the mutations are new, and 70% of the mutations are deletions. Therefore testing 1,000,000 conceptuses at 7 possibly deleted DMD sites would identify 1/4000×1/3 new mutations×0.7 mutations tested×1,000,000 conceptuses=58 affected fetuses.

In conclusion, testing for 78 cystic fibrosis mutations detects 251 affected fetuses among 1,000,000 conceptions. Using the instant invention to select and test for 32 cystic fibrosis and DMD mutations detects 298 affected fetuses among 1,000,000 conceptions.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A method of simultaneously testing for a plurality of sets of chromosomal anomalies, each set corresponding to one or more anomalies that result in a different disease to identify the largest number of tested patients who carry one or more selected tested abnormal gene sites relative to all the tested patients for each site tested in a predefined segment of the world wide population, comprising the steps of:

providing a list ordered from the most frequently occurring to the least frequently occurring chromosomal anomalies including at least two unrelated chromosomal anomalies that result in the different genetic diseases, wherein the different genetic diseases are being derived from the list beginning with the most frequently occurring chromosomal anomaly in the predefined segment of the world wide population;

selecting a threshold of the chromosomal anomaly occurrence with respect to the predefined segment of the world wide population;

selecting the at least two unrelated chromosomal anomalies for testing when the frequency of occurrence of the chromosomal anomaly in the predefined segment of the world wide population exceeds the threshold;

providing a sample of DNA for testing; and, simultaneously testing the sample for the presence of the selected at least two unrelated chromosomal anomalies, wherein said sample of DNA for testing is taken from a point in a life cycle.

2. The method of claim 1, wherein the step of providing a list beginning with the most frequently occurring to the least frequently occurring chromosomal anomalies comprises:

formulating a multiplicative product of the frequency of occurrence of the genetic disease in the predefined segment of the world wide population times a proportion of the total number of chromosomal abnormalities tested in the selected gene site.

3. The method of claim 1, wherein the step of simultaneously testing the sample for the presence of the selected at least two chromosomal anomalies, further comprises the step of:

simultaneously testing the sample for the presence of the selected at least twenty chromosomal anomalies.

4. The method of claim 1, wherein the step of simultaneously testing the sample for the presence of the selected at least two chromosomal anomalies, further comprises the step of:

simultaneously testing the sample for the presence of the selected at least thirty chromosomal anomalies.

5. The method of claim 1, wherein the step of simultaneously testing the sample for the presence of the selected at least two chromosomal anomalies, further comprises the step of:

simultaneously testing the sample for the presence of the selected at least thirty-seven chromosomal anomalies.

6. The method of claim 1, wherein the step of simultaneously testing the sample for the presence of the selected at least two chromosomal anomalies, further comprises the step of:

simultaneously testing the sample for the presence of the selected at least three chromosomal anomalies.

7. The method of claim 1, wherein the step of simultaneously testing the sample for the presence of the selected at least two chromosomal anomalies, further comprises the step of:

simultaneously testing the sample for the presence of the selected at least six chromosomal anomalies.

8. A method of simultaneously testing for a plurality of sets of chromosomal anomalies, each set corresponding to one or more anomalies and mutations that result in a different disease to identify the largest number of tested patients who carry one or more selected tested abnormal gene sites relative to all the tested patients for each site tested in a predefined segment of the world wide population, comprising the steps of:

provilding a list ordered from the most frequently occurring to the least frequently occurring chromosomal anomalies including at least two chromosomal anomalies that result in the different genetic diseases, wherein the different genetic diseases are being derived from the list beginning with the most frequently occurring chromosomal anomaly in the predefined segment of the world wide population;

selecting a threshold of the chromosomal anomaly occurrence with respect to the predefined segment of the world wide population;

selecting the at least two chromosomal anomalies for testing when the frequency of occurrence of the chromosomal anomaly and gene mutation in the predefined segment of the world wide population exceeds the threshold;

providing a sample of DNA for testing; and, simultaneously testing the sample for the presence of the selected at least two chromosomal anomalies.

9. The method of claim 8, wherein the step providing a list ordered from the most frequently occurring to the least frequently occurring chromosomal anomalies and gene mutations comprises:

formulating a multiplicative product of the frequency of occurrence of the genetic disease in the predefined segment of the world wide population times the proportion of the total number of chromosomal abnormalities and gene mutations tested in the selected gene site.

10. The method of claim 8, wherein the step of simultaneously testing the sample for the presence of the selected at least two chromosomal anomalies, further comprises the step of:

simultaneously testing the sample for the presence of the selected at least twenty chromosomal anomalies.

11. The method of claim 8, wherein the step of simultaneously testing the sample for the presence of the selected at least two chromosomal anomalies, further comprises the step of:

simultaneously testing the sample for the presence of the selected at least thirty chromosomal anomalies.

12. The method of claim 8, wherein the step of simultaneously testing the sample for the presence of the selected at least two chromosomal anomalies, further comprises the step of:

simultaneously testing the sample for the presence of the selected at least thirty-seven chromosomal anomalies.

13. The method of claim 8, wherein the step of simultaneously testing the sample for the presence of the selected at least two chromosomal anomalies, further comprises the step of:

simultaneously testing the sample for the presence of the selected at least three chromosomal anomalies.

14. The method of claim 8, wherein the step of simultaneously testing the sample for the presence of the selected at least two chromosomal anomalies, further comprises the step of:

simultaneously testing the sample for the presence of the selected at least six chromosomal anomalies.

15. The method of claim 8 wherein the at least two chromosomal anomalies are unrelated.

16. The method of claim 8, wherein each of the chromosomal anomalies in the list cause genetic disease for the predefined segment of the world wide population.

* * * * *